United States Patent
Fetzer et al.

(10) Patent No.: US 9,933,396 B2
(45) Date of Patent: Apr. 3, 2018

(54) AUTOMATED ULTRASONIC INSPECTION OF ELONGATED COMPOSITE MEMBERS USING SINGLE-PASS ROBOTIC SYSTEM

(71) Applicant: The Boeing Company, Chicago, IL (US)

(72) Inventors: Barry A. Fetzer, Renton, WA (US); Justin D. Serrill, Issaquah, WA (US)

(73) Assignee: The Boeing Company, Chicago, IL (US)

( * ) Notice: Subject to any disclaimer, the term of this patent is extended or adjusted under 35 U.S.C. 154(b) by 237 days.

(21) Appl. No.: 14/836,154

(22) Filed: Aug. 26, 2015

(65) Prior Publication Data

US 2017/0059531 A1    Mar. 2, 2017

(51) Int. Cl.
| | | |
|---|---|---|
| *G01N 29/265* | (2006.01) | |
| *G01N 29/28* | (2006.01) | |
| *G01N 29/24* | (2006.01) | |
| *G01N 29/22* | (2006.01) | |
| *G01N 29/04* | (2006.01) | |

(52) U.S. Cl.
CPC ......... *G01N 29/265* (2013.01); *G01N 29/043* (2013.01); *G01N 29/225* (2013.01); *G01N 29/28* (2013.01); *G01N 2291/0231* (2013.01); *G01N 2291/106* (2013.01); *G01N 2291/2638* (2013.01); *G01N 2291/2694* (2013.01)

(58) Field of Classification Search
CPC .. G01N 29/265; G01N 29/225; G01N 29/043; G01N 29/28; G01N 29/226; G01N 29/0645; G01N 29/04

See application file for complete search history.

(56) References Cited

U.S. PATENT DOCUMENTS

| 4,848,159 A | 7/1989 | Kennedy et al. | |
|---|---|---|---|
| 6,658,939 B2 * | 12/2003 | Georgeson ........... | G01N 29/225 73/621 |
| 7,249,512 B2 * | 7/2007 | Kennedy .............. | G01N 29/225 73/618 |
| 7,263,889 B2 | 9/2007 | Kennedy et al. | |

(Continued)

FOREIGN PATENT DOCUMENTS

CN          203365077 U    12/2013

OTHER PUBLICATIONS

Extended European Search Report dated Feb. 6, 2017 in European Application No. 16184153.1 (European counterpart of the instant patent application).

(Continued)

*Primary Examiner* — Helen Kwok
(74) *Attorney, Agent, or Firm* — Ostrager Chong Flaherty & Broitman P.C.

(57) ABSTRACT

Apparatus and methods for ultrasonic inspection of elongated composite members in a single scan pass using pulse echo phased arrays operating in a bubbler method. The system concept is fully automated by integrating an inspection probe assembly to a robot and using the robot to move the inspection probe assembly along the part (i.e., outside of an inspection tank); and by integrating tooling fixtures that move out of the way as the inspection probe assembly travels along the length of the part during the inspection. In addition, the system allows for generally elongated composite members having lengthwise variation in shape, curvature and dimensions.

21 Claims, 18 Drawing Sheets

(56) References Cited

U.S. PATENT DOCUMENTS

| | | | |
|---|---|---|---|
| 7,337,673 B2 | 3/2008 | Kennedy et al. | |
| 7,464,596 B2 * | 12/2008 | Bui | G01N 29/043 73/618 |
| 7,617,732 B2 * | 11/2009 | Bui | G01N 29/043 73/618 |
| 7,644,618 B2 | 1/2010 | Fetzer et al. | |
| 7,690,259 B2 | 4/2010 | Bui et al. | |
| 7,698,947 B2 * | 4/2010 | Sarr | G01N 29/225 73/618 |
| 7,836,768 B2 * | 11/2010 | Young | G01N 29/041 73/620 |
| 8,082,793 B2 * | 12/2011 | Sarr | G01N 29/265 73/621 |
| 8,234,942 B2 * | 8/2012 | Sarr | G01N 27/82 73/865.8 |
| 8,899,113 B2 * | 12/2014 | Fetzer | G01N 29/225 73/623 |
| 2007/0062290 A1 * | 3/2007 | Roh | G01N 29/221 73/634 |
| 2008/0302188 A1 | 12/2008 | Yabushita et al. | |
| 2015/0053015 A1 | 2/2015 | Sarr et al. | |

OTHER PUBLICATIONS

Partial European Search Report dated Nov. 18, 2016 in European Application No. 16184153.1 (European counterpart of the instant patent application).

Communication from the European Patent Office dated Oct. 13, 2017 in European Application No. 16184153.1 (European counterpart of the instant patent application).

* cited by examiner

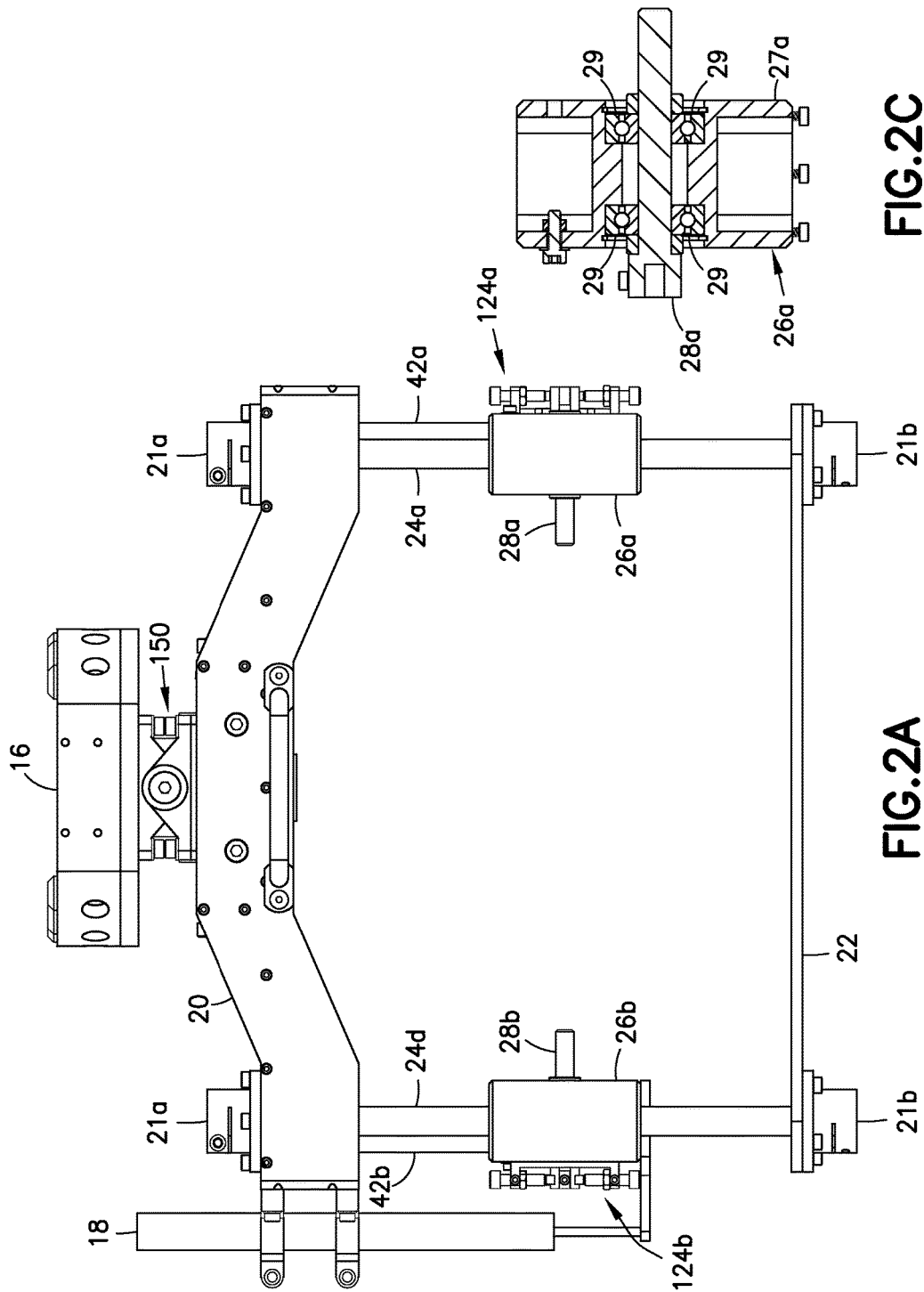

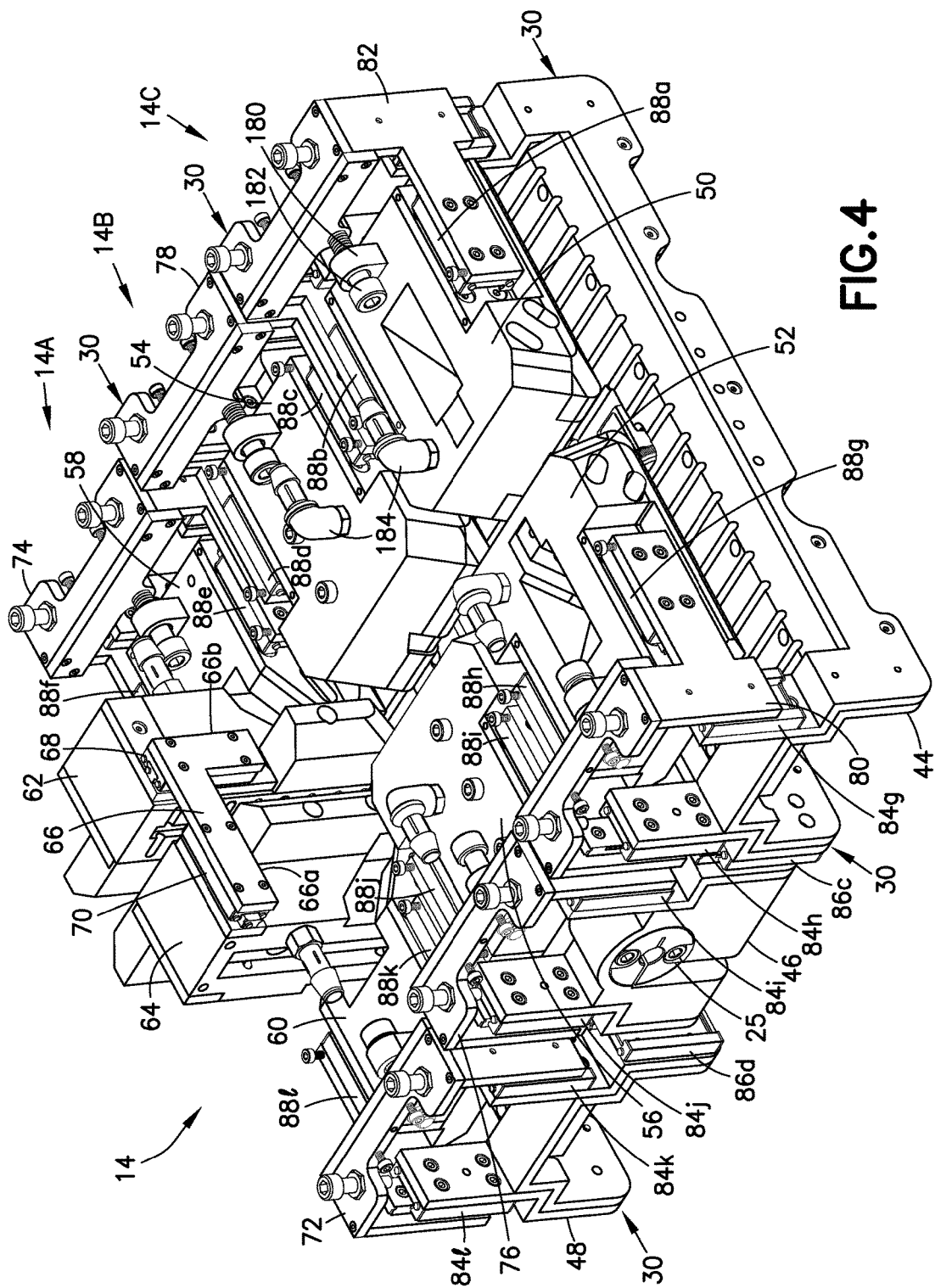

AUTOMATED ULTRASONIC INSPECTION OF ELONGATED COMPOSITE MEMBERS USING SINGLE-PASS ROBOTIC SYSTEM

BACKGROUND

This disclosure generally relates to non-destructive inspection equipment and methods, and relates more particularly to methods and apparatus for inspecting elongated members, such as stiffeners, made of composite material.

Non-destructive inspection of structures involves thoroughly examining a structure without harming the structure or requiring its significant disassembly. Non-destructive inspection is commonly used in the aircraft industry to inspect aircraft structures for any type of anomaly in the structure. Non-destructive inspection is also used in the initial fabrication of the aircraft's structural components. It is used to assure that a part was fabricated correctly and to ensure that no foreign material was embedded within the part. Inspection may be performed during manufacturing of a structure and/or after a structure has been put in service.

Non-destructive inspection (NDI) may be performed on stiffened composite parts of an aircraft. Composite parts such as fuselages and wings are frequently stiffened using elongated composite members called "stringers". These stiffeners may be made of a composite material such as carbon fiber-reinforced plastic (CFRP). As used herein, the term "elongated composite members" includes but is not limited to composite stiffeners used in the construction of fuselages and wings of aircraft, such as wing blade stiffeners and wing vent stiffeners.

More specifically, the quality of a stiffener can be determined non-destructively by ultrasonic testing. A stiffener can be inspected ultrasonically by a probe, including one or more shoes that hold respective ultrasonic transducer arrays, that is moved incrementally along the length of the stiffener. As the probe is being moved, the transducer arrays may operate in pulse/echo mode to generate pulsed ultrasonic waves, which propagate into the stiffener. Reflected ultrasonic waves are returned to and detected by the ultrasonic transducer arrays to provide data indicative of the presence of anomalies in the stiffener. Data acquired by the ultrasonic transducer arrays is typically processed by a computer system, and the processed data may be presented to a user via a computer monitor. A data acquisition device and data handling software may be used for collection and display of inspection data, such as displaying the data on a computer monitor as an image representation of the structure under inspection, such as a stringer, supplemented with corresponding color and/or graphical data of the inspection to permit examination by a qualified inspector.

Automated inspection systems typically employ a manipulator (e.g., overhead gantry, multi-axis scanner, or robot) that scans an NDI end effector along the part being inspected. For single-sided inspection methods, such as pulse echo ultrasonic inspection, a single-arm robotic device having multiple degrees of freedom may be used to position and move an NDI end effector, such as a pulse echo ultrasonic inspection device, attached to the end of the robot arm.

Some stiffeners incorporated in aircraft wings are inspected in large immersion tanks, which can have an impact on overall manufacturing throughput and on the required factory floor space for the inspection system. In a feed-through immersion system, stiffeners may move through the inspection probes by keeping the probes relatively stationary inside a small immersion tank. This process requires the system to be twice as long as the part because the part must be fed into one side of the immersion tank and then exit the other side.

It would be advantageous to provide a single-pass NDI system designed so that the part can remain stationary during inspection, thereby reducing the inspection time required and the amount of factory space occupied by the inspection station.

SUMMARY

The subject matter disclosed in detail below is directed to methods and apparatus for ultrasonic inspection of elongated composite members in a single scan pass using pulse echo phased arrays operating in a bubbler method. The system concept is fully automated by integrating an inspection probe assembly to a robot and using the robot to move the inspection probe assembly along the part (i.e., outside of an inspection tank); and by integrating tooling fixtures that move out of the way as the inspection probe assembly travels along the length of the part during the inspection. The embodiments disclosed in detail below enable high production rates by providing a single-pass NDI system designed to inspect a part while it is stationary. This feature will reduce the amount of factory space used. In addition, incorporating robotic technology into the inspection provides a fully automated inspection to reduce or eliminate operator fatigue.

In addition, the system allows for elongated composite members having lengthwise variation in shape, curvature and dimensions. The ultrasonic inspection apparatus disclosed herein has enough degrees of freedom to allow for local part movements in the roll, pitch, yaw, lateral and elevation directions while still maintaining proper probe alignment to the part.

For the purpose of illustration and explanation, apparatus and methods for ultrasonic inspection of a generally T-shaped wing blade stiffener in a single scan pass (hereinafter "single pass") will be described in detail hereinafter. However, some of the principles and concepts embodied by the apparatus disclosed hereinafter can be applied in ultrasonic inspection of other elongated composite members having profiles that are not generally T-shaped.

In the case where the elongated composite member is a wing blade stiffener comprising a flange intersected by a web to form radiused portions (a.k.a. "radii") on both sides of the intersection, an ultrasonic inspection tool head is provided that comprises two phased linear ultrasonic transducer arrays for inspecting the flange, two phased linear ultrasonic transducer arrays for inspecting the web, and two phased curved ultrasonic transducer arrays for inspecting the radiused portions.

Conventional composite structure cured with hard tooling results in composite radii that are well defined and repeatable. In contrast, the composite radii formed using soft tooling are not always well defined and may vary from part to part. In some cases, dimensional or contour variations may be greater than those that would result from using hard tooling. These larger variations make reliable inspection more difficult. In view of the deviation from circularity of soft-tooled composite radii, the term "radius" as used hereinafter should be construed non-strictly to include non-circular profiles.

The system for inspecting blade stiffeners is designed to allow the position and orientation of the ultrasonic inspection tool head to adjust for changing web-flange angle, web height, flange width, thickness, or contour in an elevational or lateral direction (e.g., curvature to reflect the shape of a wing skin). In a preferred embodiment, the system allows the web-flange angle to change by ±15°. In one possible implementation, a linear variable differential transformer (LVDT) can be integrated into the inspection probe assembly. The output from the LVDT is used to dynamically control robot movement, thereby accommodating large changes in the contour or curvature of the blade stiffener along its length.

One aspect of the subject matter disclosed in detail below is an apparatus comprising: a frame; first and second rotatable shafts which are mutually coaxial and rotatable relative to the frame; and a probe housing assembly clamped to the first and second rotatable shafts, wherein the probe housing assembly comprises: a first probe platform clamped to the first and second rotatable shafts; a second probe platform; first and second linear slides configured to translatably couple the second probe platform to the first probe platform; a third probe platform; and third and fourth linear slides configured to translatably couple the third probe platform to the first probe platform. In embodiments wherein the frame comprises first through fourth guide shafts, the apparatus further comprises a first bearing block assembly translatably coupled to the first and second guide shafts, and a second bearing block assembly translatably coupled to the third and fourth guide shafts, wherein the first rotatable shaft is rotatably coupled to the first bearing block assembly, and the second rotatable shaft is rotatably coupled to the second bearing block assembly. The apparatus may further comprise a gimbal assembly, wherein the frame is mounted to the gimbal assembly, and the gimbal assembly comprises a connector configured to be attached to a connector of a robot, a revolute joint supported by the connector, a thrust bearing, and fifth and sixth linear slides configured to translatably couple the thrust bearing to the revolute joint.

In accordance with some embodiments, the apparatus described in the preceding paragraph further comprises: a first web probe translatably coupled to the third probe platform for translation along first and second axes which are mutually perpendicular, the first web probe comprising a first linear ultrasonic transducer array; a second web probe translatably coupled to the third probe platform for translation along third and fourth axes which are mutually perpendicular, the second web probe comprising a second linear ultrasonic transducer array which is parallel to the first linear ultrasonic transducer array. The first web probe may be rotatably coupled to the third probe platform for rotation about a fifth axis which is perpendicular to the first and second axes, and the second web probe may be rotatably coupled to the third probe platform for rotation about a sixth axis which is perpendicular to the third and fourth axes. In one possible implementation, the apparatus further comprises: an L-shaped member comprising first and second legs that form a right angle; a fifth linear slide configured to translatably couple the first leg of the L-shaped member to the first web probe to enable translation along a length of the first leg; and a second linear slide configured to translatably couple the second leg of the L-shaped member to the first web probe to enable translation along a length of the second leg, wherein the first and second linear ultrasonic transducer arrays stay mutually parallel and displace relative to each other during rotation in tandem about the first and second axes respectively.

In accordance with the same embodiments, the apparatus further comprises: a first radius probe translatably coupled to the second probe platform for translation along first and second axes which are mutually perpendicular, the first radius probe comprising a first curved ultrasonic transducer array; and a second radius probe translatably coupled to the second probe platform for translation along third and fourth axes which are mutually perpendicular, the second radius probe comprising a second curved ultrasonic transducer array.

In accordance with the same embodiments, the apparatus further comprises: a third linear ultrasonic transducer array housed in the first probe platform; and a dry acoustic couplant material separated from the first linear ultrasonic transducer array by a gap, wherein the probe housing assembly further comprises: a dry acoustic couplant housing translatably coupled to the first probe platform for translation along first and second axes which are mutually perpendicular, the dry acoustic couplant housing supporting the dry acoustic couplant material. Optionally a second linear ultrasonic transducer array may housed in the first probe platforms.

In accordance with some embodiments, the apparatus further comprises: a first web probe translatably coupled to one of the first through third probe platforms for translation along first and second axes which are mutually perpendicular, the first web probe comprising a first linear ultrasonic transducer array; a second web probe translatably coupled to the one of the first through third probe platforms for translation along third and fourth axes which are mutually perpendicular, the second web probe comprising a second linear ultrasonic transducer array which is parallel to the first linear ultrasonic transducer array; a first radius probe translatably coupled to another of the first through third probe platforms for translation along fifth and sixth axes which are mutually perpendicular, the first radius probe comprising a first curved ultrasonic transducer array; and a second radius probe translatably coupled to the another of the first through third probe platforms for translation along seventh and eighth axes which are mutually perpendicular, the second radius probe comprising a second curved ultrasonic transducer array.

The apparatus described in the preceding paragraph may further comprise: a third linear ultrasonic transducer array housed in a further one of the first through third probe platforms; and a dry acoustic couplant material separated from the third linear ultrasonic transducer array by a gap, wherein the probe housing assembly further comprises: a dry acoustic couplant housing translatably coupled to the further one of the first through third probe platforms for translation along ninth and tenth axes which are mutually perpendicular, the dry acoustic couplant housing supporting the dry acoustic couplant material.

The first, second and third linear ultrasonic transducer arrays and the first and second curved ultrasonic transducer arrays are arranged so that the first and second linear ultrasonic transducer arrays can interrogate a web portion of an elongated composite member having a generally T-shaped profile, while the first and second curved ultrasonic transducer arrays can interrogate respective radiused portions of the elongated composite member, and the third linear ultrasonic transducer array can interrogate a first flange portion of the elongated composite member in a single pass. Optionally a fourth linear ultrasonic transducer array may be provided for interrogating a second flange portion of the elongated composite member.

Another aspect of the subject matter disclosed in detail below is an apparatus comprising: a probe housing assembly; a first web probe rotatably coupled to the probe housing assembly for rotation about a first axis, the first web probe comprising a first linear ultrasonic transducer array; a second web probe rotatably coupled to the probe housing assembly for rotation about a second axis which is parallel to the first axis, the second web probe comprising a second linear ultrasonic transducer array which is parallel to the first linear ultrasonic transducer array; an L-shaped member comprising first and second legs that form a right angle; a first linear slide configured to translatably couple the first leg of the L-shaped member to the first web probe to enable translation along a length of the first leg; and a second linear slide configured to translatably couple the second leg of the L-shaped member to the first web probe to enable translation along a length of the second leg, wherein the first and second linear ultrasonic transducer arrays stay mutually parallel and displace relative to each other during rotation in tandem about the first and second axes respectively. In accordance with some embodiments, the probe housing assembly comprises: a left pivot support carriage which is rotatably coupled to the first web probe; a first slide bracket assembly; third and fourth linear slides configured to translatably couple the first slide bracket assembly to the left pivot support carriage; a right pivot support carriage which is rotatably coupled to the second web probe; a second slide bracket assembly; and fifth and sixth linear slides configured to translatably couple the second slide bracket assembly to the right pivot support carriage; wherein the left and right pivot support carriages are slidable along third and fourth axes respectively, the third and fourth axes being perpendicular to the first and second axes. The probe housing assembly may further comprise: a web probe platform; seventh and eighth linear slides configured to translatably couple the first slide bracket assembly to the web probe platform; and ninth and tenth linear slides configured to translatably couple the second slide bracket assembly to the web probe platform, wherein the first and second slide bracket assemblies are slidable along fifth and sixth axes respectively, the fifth axis being perpendicular to the first and third axes, and the sixth axis being perpendicular to the second and fourth axes.

The apparatus described in the preceding paragraph may further comprise a frame and first and second rotatable shafts which are mutually coaxial and rotatable relative to the frame, wherein the probe housing assembly is clamped to the first and second rotatable shafts. In accordance with some embodiments, the frame comprises first through fourth guide shafts, the apparatus further comprising a first bearing block assembly translatably coupled to the first and second guide shafts, and a second bearing block assembly translatably coupled to the third and fourth guide shafts, wherein the first rotatable shaft is rotatably coupled to the first bearing block assembly, and the second rotatable shaft is rotatably coupled to the second bearing block assembly.

The probe housing assembly may further comprise: a flange probe platform clamped to the first and second rotatable shafts; eleventh and twelfth linear slides configured to translatably couple the web probe platform to the flange probe platform, the apparatus further comprising a third linear ultrasonic transducer array housed in the flange probe platform. In embodiments wherein the apparatus further comprises a dry acoustic couplant material separated from the third linear ultrasonic transducer array by a gap, the probe housing assembly may further comprise: a dry acoustic couplant housing which supports the dry acoustic couplant material; a third slide bracket assembly; fifteenth and sixteenth linear slides configured to translatably couple the third slide bracket assembly to the dry acoustic couplant housing; and seventeenth and eighteenth linear slides configured to translatably couple the third slide bracket assembly to the radius probe platform. The probe housing assembly may further comprise: a radius probe platform, and thirteenth and fourteenth linear slides configured to translatably couple the radius probe platform to the flange probe platform, in which case the apparatus further comprises first and second radius probes translatably coupled to the radius probe platform, wherein the first and second radius probes comprise respective curved ultrasonic transducer arrays. In addition, the probe housing assembly may further comprise: a third slide bracket assembly; fifteenth and sixteenth linear slides configured to translatably couple the third bracket assembly to the first radius probe; seventeenth and eighteenth linear slides configured to translatably couple the third slide bracket assembly to the radius probe platform; a fourth slide bracket assembly; nineteenth and twentieth linear slides configured to translatably couple the fourth bracket assembly to the second radius probe; and twenty-first and twenty-second linear slides configured to translatably couple the fourth slide bracket assembly to the radius probe platform.

A further aspect of the disclosed subject matter is a method for automated ultrasonic inspection of a stationary elongated composite member in a single pass, comprising: supporting the elongated composite member using a multiplicity of holding fixtures disposed at intervals along a length of the elongated composite member, each holding fixture having an extended position in which the elongated composite member is supported and a retracted position in which the holding fixture is separated from the elongated composite structure; moving an inspection probe assembly along a length of the elongated composite member from one end of the elongated composite member to another end of the elongated composite member, the probe assembly comprising a multiplicity of ultrasonic transducer arrays; concurrently ultrasonically inspecting web, flange and radiused portions of the elongated composite member using the multiplicity of ultrasonic transducer arrays as the inspection probe assembly moves along the length of the elongated composite member; moving each holding fixture to its retracted position in sequence to allow the probe assembly to pass by; and extending each retracted holding fixture back to its extended position after the probe assembly has passed by. This method may further comprise: adjusting the positions of the multiplicity of ultrasonic transducer arrays to take into account variations in the shape and location of the elongated composite member along its length as the inspection probe assembly moves along the length of the elongated composite member. In particular, the respective angles of first and second linear ultrasonic transducer arrays can be adjusted as an angle between web and flange portions of the elongated composite member changes along its length, while an elevation of an end effector assembly that supports the inspection probe assembly is adjusted as a curvature of the elongated composite member in an elevation direction changes along its length.

Other aspects of methods and apparatus for inspecting elongated composite members are disclosed below.

BRIEF DESCRIPTION OF THE DRAWINGS

FIG. 2A is a diagram representing an elevational view of an end effector assembly incorporated in the tool head depicted in FIG. 2.

FIG. 2C is a diagram representing a sectional view taken along a plane that bisects a rotatable shaft rotatably coupled to the bearing block assembly depicted in FIG. 2B.

FIG. 4 is a diagram representing an isometric view of an inspection probe assembly incorporated in the tool head depicted in FIG. 2.

In FIG. 9A, the section is taken through a first linear ultrasonic transducer array; in FIG. 9B, the section is taken through a second linear ultrasonic transducer array.

Reference will hereinafter be made to the drawings in which similar elements in different drawings bear the same reference numerals.

DETAILED DESCRIPTION

Embodiments of apparatus and methods for ultrasonic inspection of elongated composite members will now be described with reference to the inspection of generally T-shaped wing blade stiffeners. However, the apparatus and methods disclosed herein may also be used to ultrasonically inspect composite stiffeners having other profiles and elongated composite members other than stiffeners.

Figure 1:
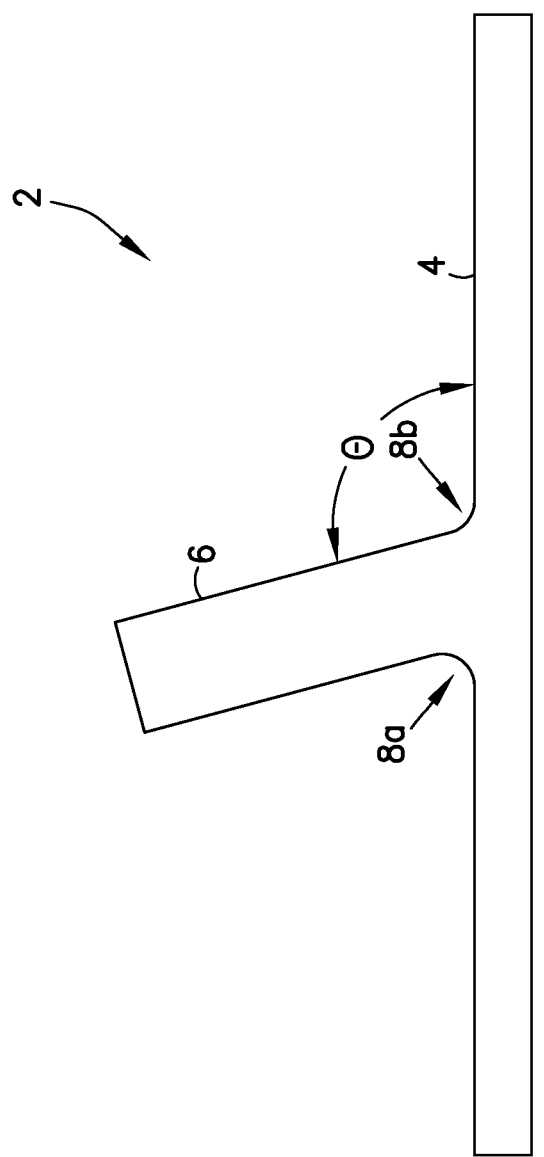
FIG. 1 is a diagram showing a representative profile of a composite blade stiffener. The profile typically varies from a true T-shape as the web angle diverges from perpendicular along the length of the blade stiffener.

FIG. 1 is a diagram showing a representative profile of a composite blade stiffener 2 comprising a flange 4 and a web 6 that intersects flange 4. In the area of the intersection, the blade stiffener has left and right radiused portions 8a and 8b. Although not apparent from FIG. 1, it should be appreciated that blade stiffener 2 may have a profile that varies along its length. At some locations, the profile may be T-shaped; at other locations the profile may vary from T-shaped, e.g., the web-flange angle θ diverges from 90° along the length of blade stiffener 2 (as depicted in FIG. 1). For example, the web-flange angle θ may change by ±15°. A blade stiffener profile having a web angle in this range will be referred to herein as a "generally T-shaped blade stiffener".

Figure 2:
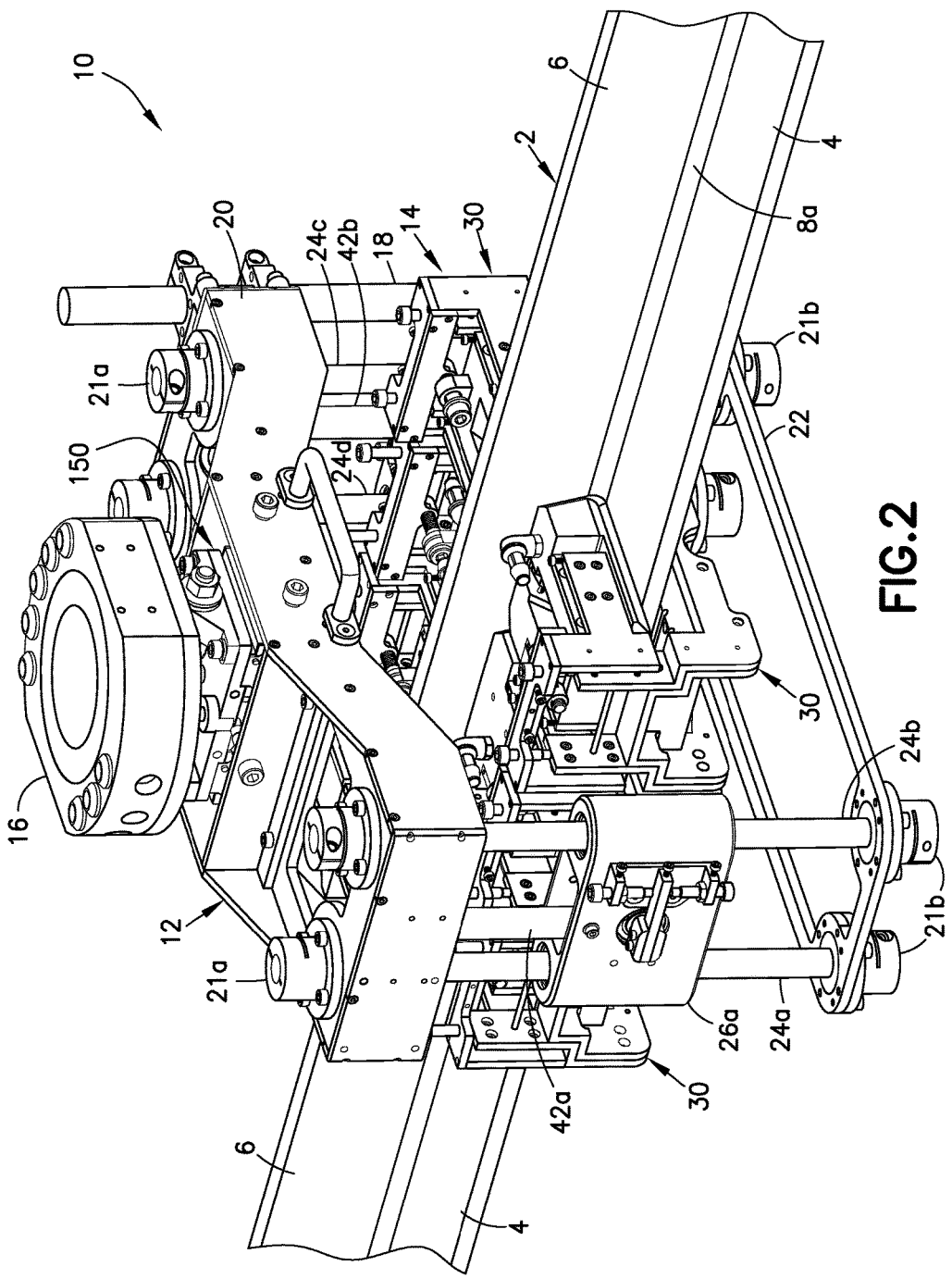
FIG. 2 is a diagram representing an isometric view of an ultrasonic inspection tool head in accordance with one embodiment, mounted to a generally T-shaped blade stiffener.

The blade stiffener 2 can be inspected in one pass using an ultrasonic inspection tool head 10 of the type depicted in FIG. 2. The ultrasonic inspection tool head 10 is mounted to the blade stiffener 2. In accordance with the embodiment depicted in FIG. 2, the ultrasonic inspection tool head 10 comprises an end effector assembly 12 and an inspection probe assembly 14 that is carried by the end effector assembly 12. The end effector assembly 12 comprises a quick-release tool-side connector plate 16, an upper frame 20, and a gimbal assembly 150 which couples the upper frame 20 to the tool-side connector plate 16. As will be discussed later with reference to FIG. 3, tool-side connector plate 16 is connected to a compatible robot-side connector plate 114.

During a single scan pass, the ultrasonic inspection tool head 10 travels along the length of the blade stiffener 2 from one end to the other end, scanning the flange 4, the web 6 and the radiused portions (only radiused portion 8a is visible in FIG. 2). In accordance with one embodiment, the inspection probe assembly 14 comprises two phased linear ultrasonic transducer arrays for inspecting the flange 4, two phased linear ultrasonic transducer arrays for inspecting the web 6, and two phased curved ultrasonic transducer arrays for inspecting the radiused portions 8a, 8b, which ultrasonic transducer arrays are not visible in FIG. 2. The inspection probe assembly 14 further comprises a probe housing assembly 30 which adjustably supports the ultrasonic transducer arrays, as will be explained in more detail later.

Still referring to FIG. 2, the end effector assembly 12 further comprises four guide shafts 24a-24d each having one end fixedly coupled (i.e., attached) to the upper frame 20 by means of respective shaft mounts 21a, and a lower frame 22 fixedly coupled to the other ends of guide shafts 24a-24d by means of respective shaft mounts 21b. In a preferred embodiment, the axes of guide shafts 24a-24d are all parallel to a Z axis in the frame of reference of the end effector assembly 12. The end effector assembly 12 further comprises a pair of bearing block assemblies 26a and 26b (best seen in FIG. 2A) which are coupled to the upper frame 20 by means of respective constant force spring assemblies 42a and 42b (for reasons discussed below with reference to FIG. 2B). In addition, bearing block assembly 26a is translatably coupled to guide shafts 24a and 24b by means of respective pairs of linear bearings (not shown in FIG. 2); bearing block assembly 26b (visible in FIG. 2A) is translatably coupled to guide shafts 24c and 24d by means of respective pairs of linear bearings (not shown). The bearing block assemblies 26a and 26b (which support the inspection probe assembly 14) can translate in tandem in the Z direction in the frame of reference of the end effector assembly 12 while the constant force spring assemblies 42a and 42b exert lifting forces thereon. As best seen in FIG. 2A, the displacement of bearing block assembly 26b in the Z direction is measured by an LVDT 18 which is integrated in the end effector assembly 12. The displacements of the bearing block assemblies 26a and 26b will be equal.

As seen in FIG. 2A, the bearing block assembly 26a comprises a rotatable shaft 28a, while the bearing block assembly 26c comprises a rotatable shaft 28b. The rotatable shafts 28a and 28b have a common axis of rotation, which may be treated as the Y axis (perpendicular to the Z axis) in the frame of reference of the end effector assembly 12. The probe housing assembly 30 of the inspection probe assembly 14 (best seen in FIG. 2) is clamped to the rotatable shafts 28a and 28b.

FIG. 2C is a diagram representing a sectional view taken along a plane that bisects rotatable shaft 28a. The bearing block assembly 26a comprises a bearing block 27 in which a pair of coaxial ball bearings 29a and 29b are seated. The rotatable shaft 28a is rotatably coupled to the bearing block 27 by means of ball bearings 29a and 29b. The bearing block assembly 26b has a similar structure. As a result of this design, the probe housing assembly 30, which is clamped to rotatable shafts 28a and 28b, can rotate about the Y axis of the end effector assembly 12.

As seen in FIG. 2A, each bearing block assembly 26a, 26b comprises a respective shaft rotation limit assembly 124a, 124b which limits the range of rotation of a respective rotatable shaft 28a, 28b. The structure of shaft rotation limit assembly 124a is shown in detail in FIG. 2B. The other shaft rotation limit assembly 124b has a similar structure. The shaft rotation limit assembly 124a comprises a paddle 126 having a proximal end fastened to one end of rotatable shaft 28a and a distal end which is free to rotate about the axis of rotatable shaft 28a between respective angular position limits. The shaft rotation limit assembly 124a further comprises a pair of cap screws 128a and 128b (FIG. 2B) which can be loosened or tightened to adjust the angular position limits. The rotatable shaft 28a reaches one angular position limit when the upper surface of the distal end of paddle 126 abuts the end of cap screw 128a and reaches the other angular position limit when the lower surface of the distal end of paddle 126 abuts the end of cap screw 128b.

Figure 2B:
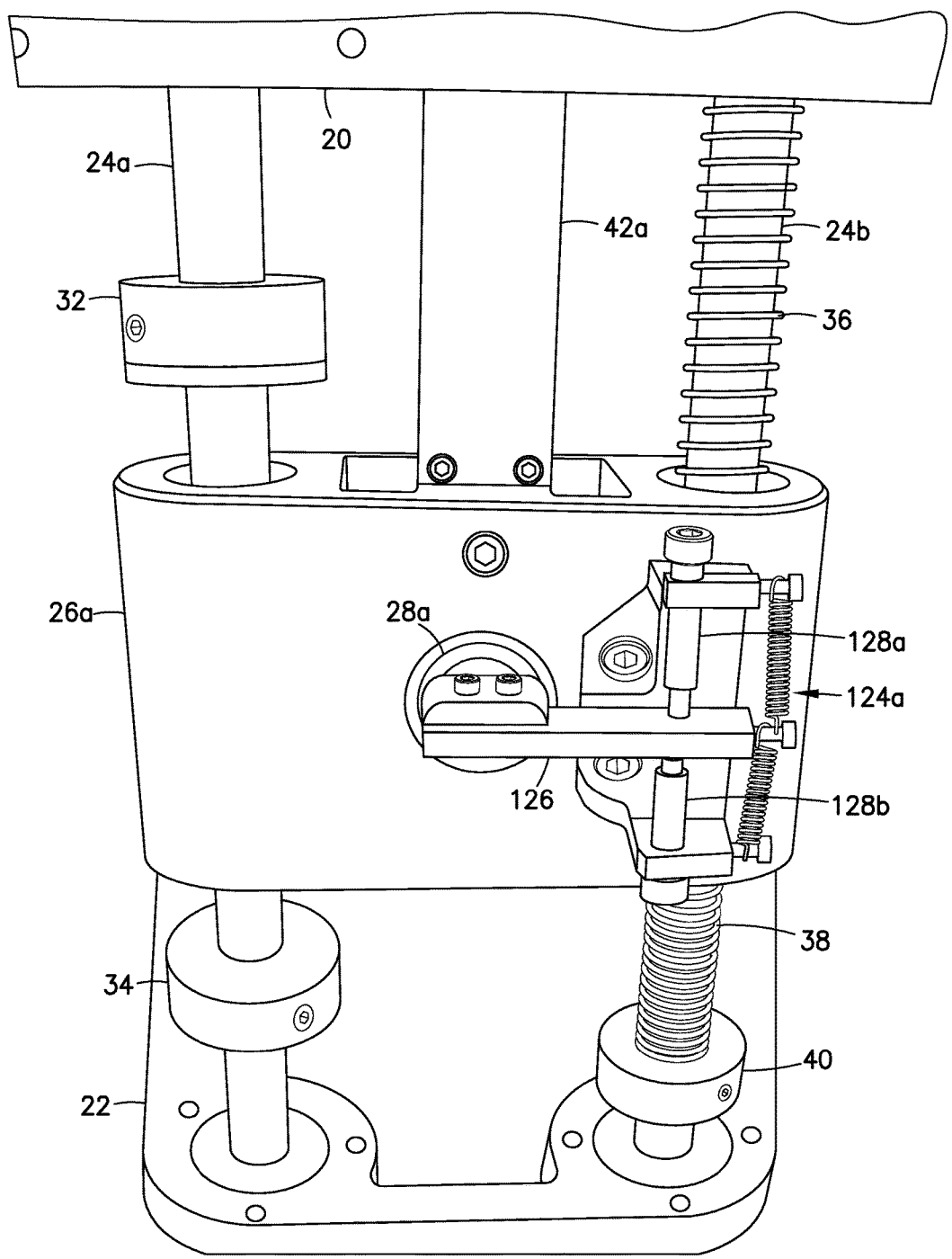
FIG. 2B is a diagram showing portions of an end effector assembly having a bearing block assembly translatably coupled thereto, which components are incorporated in the tool head depicted in FIG. 2.

As further seen in FIG. 2B, the displacement of bearing block assembly 26a along guide shafts 24a and 24b is limited by upper shaft collar 32 and lower shaft collar 34, which are respectively clamped to guide shaft 24a. In one implementation, the upper and lower shaft collars 32 and 34 are positioned so that the bearing block assembly 26a is able to travel along guide shafts 24a and 24b ±1 inch from a neutral position. This provides a ±1-inch tolerance in the local inspection zone. Within this range of displacement, upward displacement is resisted by an upper compression spring 36 wound around the guide shaft 24b, while downward displacement is resisted by a lower compression spring 38 wound around the guide shaft 24b and seated on shaft collar 40 clamped to guide shaft 24b. The upper and lower compression springs 36 and 38 are used to center the inspection probe assembly in the neutral position when on an elongated composite member.

In addition, respective constant force spring assemblies 42a and 42b (only constant force spring assembly 42a is visible in FIG. 2B) apply a constant force regardless of travel distance that counters the weight of the inspection probe assembly 14 and allows the latter to "float" in the middle of the guide shafts 24a-24d. This ensures that the inspection probe assembly 14 applies very little force to the top of the blade stiffener as the assembly travels along the length of the stiffener. As is well known in the art, each constant force spring assembly 42a, 42b comprises a rolled ribbon of spring steel designed so that the spring is relaxed when it is fully rolled up or wound on a reel. In the embodiment depicted in FIG. 2B, the reels (not visible) are bolted to the upper frame 20 of the end effector assembly 12 and the springs are attached to the bearing block assemblies 26a and 26b on respective sides of the inspection probe assembly 14.

Figure 3:
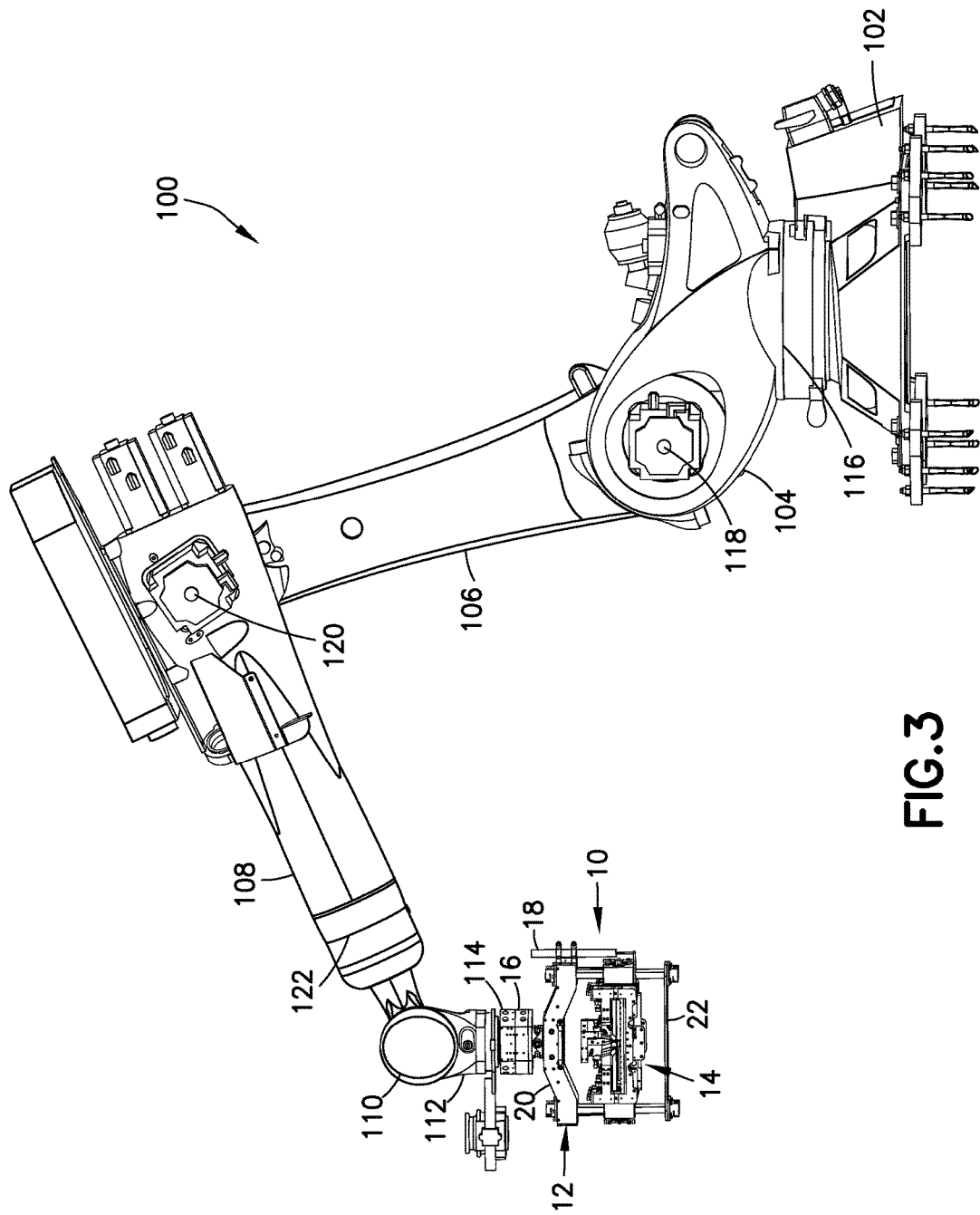
FIG. 3 is a diagram representing an elevational view of the ultrasonic inspection tool head depicted in FIG. 2 mounted to a robot.

FIG. 3 shows an automated system for inspecting an elongated composite member such as a blade stiffener in which the ultrasonic inspection tool head 10 is mounted to a robot 100. Although not shown in FIG. 3, the ultrasonic probes incorporated in the ultrasonic inspection tool head 10 will be electrically connected to a data acquisition system (also not shown in FIG. 3) by means of electrical cables (not shown in FIG. 3) and will be in fluid communication with a source of liquid acoustic couplant (e.g., water) by means of hoses.

The ultrasonic inspection tool head 10 is attached to the robot 100 by attaching the tool-side connector plate 16 to a connector 114 of the robot 100. As the ultrasonic inspection tool head 10 is moved along the elongated composite member being inspected, data is sent to the data acquisition system for processing. Typically, the robot 100 is automatically controlled to move the ultrasonic inspection tool head 10 in a lengthwise direction along the elongated composite member, while the data acquisition system generates images of the surface of the elongated composite member to map the inspection probes' responses. The robot 100 could be used to inspect any number of elongated composite members in a variety of industries where detection of flaws or defects in the structure is required, such as in the aircraft, automotive, or construction industries. In particular, if the ultrasonic inspection tool head 10 is of the type shown in FIG. 2, the robot 100 could be used to inspect stiffeners of the type shown in FIGS. 1 and 2.

The robot 100 has multi-axis movement capabilities and uses software support to generate a three-dimensional profile to be used for measurement and inspection of parts. In particular, the robot 100 shown in FIG. 3 comprises a robot base 102, a carousel 104, a rocker 106 (a.k.a. pivot arm), an extension arm 108, a robot hand 110, and a member 112 to which the connector 114 is attached. The robot base 102 and carousel 104 are rotatably coupled by a pivot 116. The carousel 104 and rocker 106 are rotatably coupled by a pivot 118. The rocker 106 and extension arm 108 are rotatably coupled by a pivot 120. The rocker extension arm 108 and robot hand 110 are rotatably coupled by a pivot 122. The combination of these components provides multiple degrees of freedom, which in turn allows the ultrasonic inspection tool head 10 to be moved to different locations and in different directions. The robot 100 includes one or more positional sensors (not shown) at, or otherwise associated with, each of the pivots that provide positional data (X, Y, and Z in three-dimensional space) to the data acquisition system for accurately locating the probes. In addition, the ultrasonic inspection tool head 10 could include various numbers of sensors (e.g., one or more) for acquiring positional data. The probes provide ultrasonic data indicative of the structure being inspected. As such, the robot 100 provides an accurate location of any defects using positional data and ultrasonic data acquired during inspection of an elongated composite member. An example of a robot 100 that could be employed with the probe shown in FIG. 2 is robot Model KR-150 manufactured by Kuka Roboter GmbH (Augsburg, Germany), although any robot or other manipulator capable of carrying an ultrasonic inspection tool head and communicating with a data acquisition system could be used.

The data acquisition system may be capable of generating various images, including A-scan, B-scan, and C-scan images of elongated composite members based on data collected by the positional sensors and ultrasonic probes. Furthermore, the data acquisition system may be capable of generating a three-dimensional point cloud based on the data acquired by the positional sensors and the ultrasonic probes. Thus, a stream of positional data may be mapped to a stream of ultrasonic data to generate the point cloud. The ultrasonic data may include, among other information, data regarding anomalies, defects, irregularities, or other imperfections in the inspected structure. The data acquisition system typically includes a processor or similar computing device operating under the control of imaging software so that any defects in the inspected structure may be presented on a display screen. The processor could be embodied by a computer such as a desktop, laptop, or portable processing device capable of processing the data generated by the positional sensors and ultrasonic probes and creating an image of the scanned data that is shown on a display such as a monitor or other viewing device. The data acquisition system may generate images of the data and also allow a user to store and edit previously created images. Therefore, a permanent record of the images may be kept for future use or record keeping. However, it is understood that the data acquisition system need not generate images, as the data acquisition system could mathematically collect and analyze positional and ultrasonic data that a technician could use to characterize and locate a flaw based on the data.

The robot 100 is typically in communication with the data acquisition system to process the data acquired by the positional sensors and ultrasonic probes and to display the processed data. In many cases, communications cable(s) (not shown in FIG. 3) transmit data between the robot 100 and the data acquisition system. In other embodiments, the data may be transmitted between the robot 100 and the data acquisition system via wireless communications. The robot 100 may be directly connected to the processor, or indirectly connected, such as via a network. In further embodiments, the data acquisition system may be located proximate to the robot 100, such that remote connections between the robot and data acquisition system are not necessary.

As previously described with reference to FIG. 2, the end effector assembly 12 comprises a gimbal assembly 150 which couples upper frame 20 to the tool-side connector plate 16. The gimbal assembly 150 is designed to enable the end effector frame assembly, comprising upper frame 20, lower frame 22 and guide shafts 24a-24d, to rotate about X and Z axes (the X axis being the longitudinal axis of the elongated composite member being inspected) and translate along a Y axis relative to the tool-side connector plate 16.

Figure 3A:
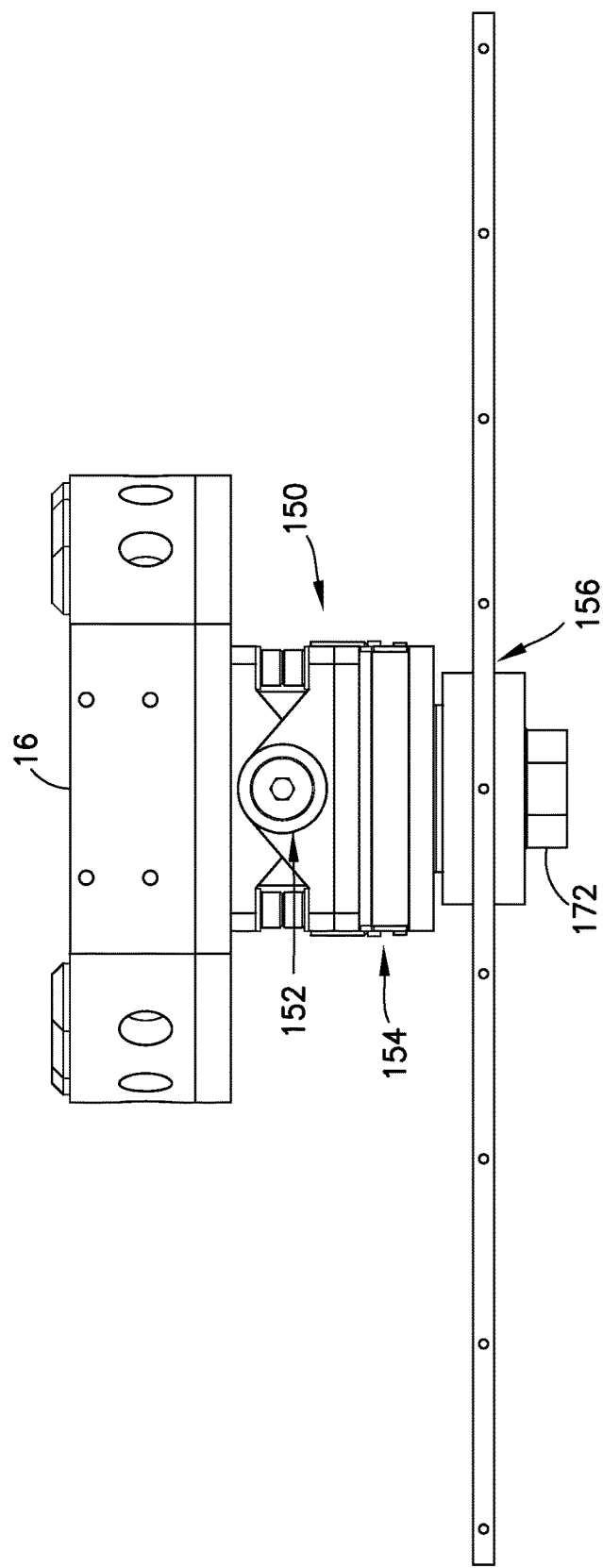
FIG. 3A is a diagram representing an elevational view of a gimbal assembly incorporated in the tool head depicted in FIG. 2.

FIG. 3A shows an elevational view of the gimbal assembly 150. The gimbal assembly 150 comprises: (1) a pivot joint 152 that allows the end effector to rotate around the X axis; (2) a pair of linear slides 154 that allow the end effector to translate along the Y axis within a specified range (e.g., ±1 inch; and (3) a rotational joint 156 that allows the end effector to rotate around the Z axis.

Figure 3B:
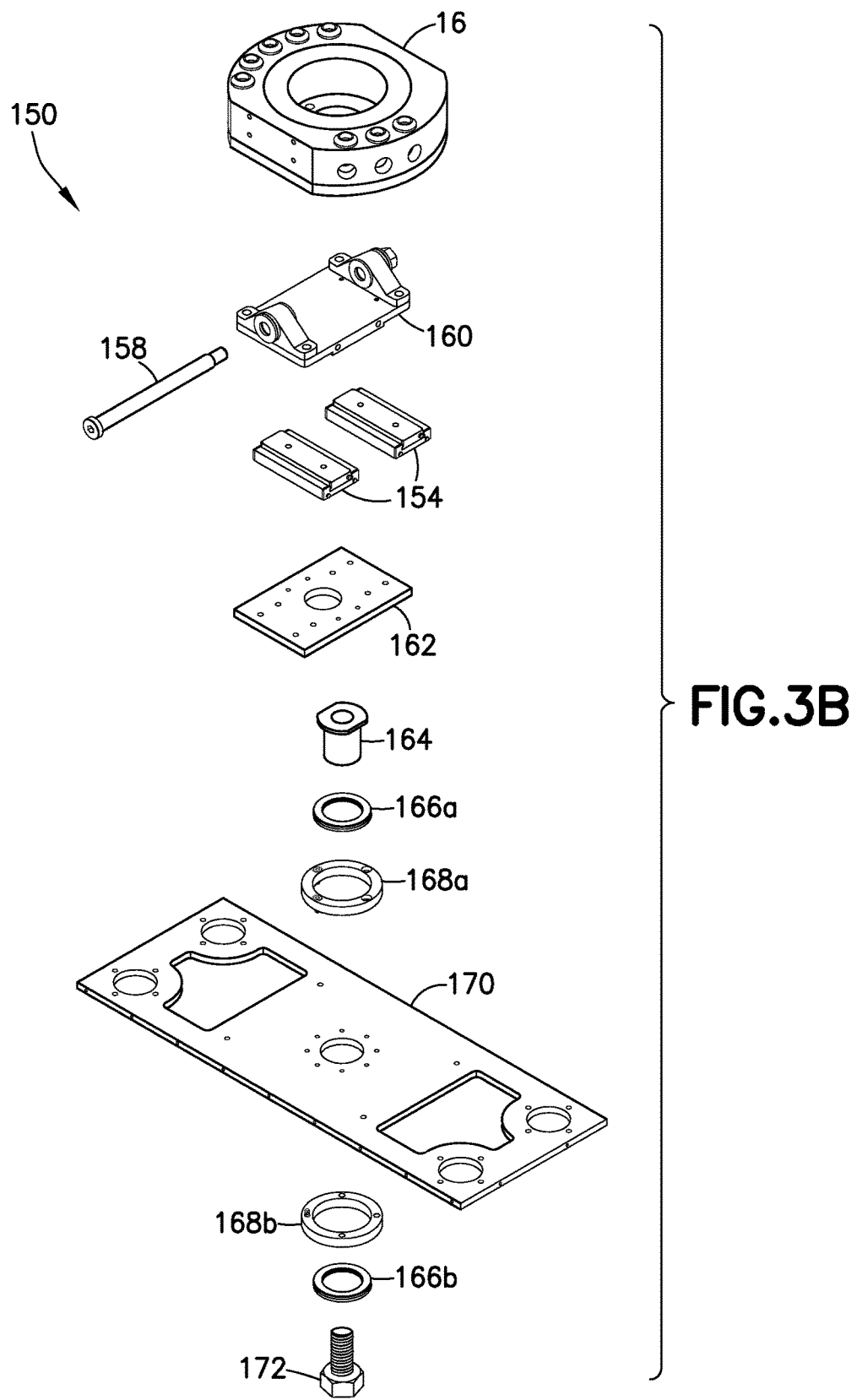
FIG. 3B is a diagram representing an exploded view of the gimbal assembly depicted in FIG. 3A.

FIG. 3B shows an exploded view of the gimbal assembly 150 depicted in FIG. 3A. The gimbal assembly 150 comprises a pivot bushing 160 which is rotatably coupled to the tool-side connector by means of a pivot pin 158 to form the pivot joint 152. The gimbal assembly 150 further comprises a linear slide mounting plate 162, which is translatably coupled to the pivot bushing 160 by means of a pair of linear slides 154. An end effector base plate 170 (which is part of upper frame 20 seen in FIG. 2) is rotatably coupled to linear slide mounting plate 162 by means of the rotational joint 156 indicated in FIG. 3A. As seen in FIG. 3B, the rotational joint 156 comprises a threaded bushing 164 (which is fastened to linear slide mounting plate), an upper thrust bearing 166a, an upper thrust bearing locating ring 168a, a lower thrust bearing 166b, a lower upper thrust bearing locating ring, and bolt 172.

The apparatus described above comprises an end effector frame that is rotatable about the X and Y axes and translatable along the Y axis. As previously described, the probe housing assembly 30 is rotatably coupled to the end effector frame by means of a pair of rotatable shafts 28a and 28b having a common axis of rotation which is parallel to the Y axis. Thus the inspection probe assembly 14 is effectively rotatable about the X, Y and Z axes and translatable in the Y direction. In addition, as will now be explained in detail, the probe housing assembly 30 comprises means for allowing the respective probes to adjust their positions and orientations to take into account variations in size, shape and curvature of the elongated composite member being inspected.

Figure 5:
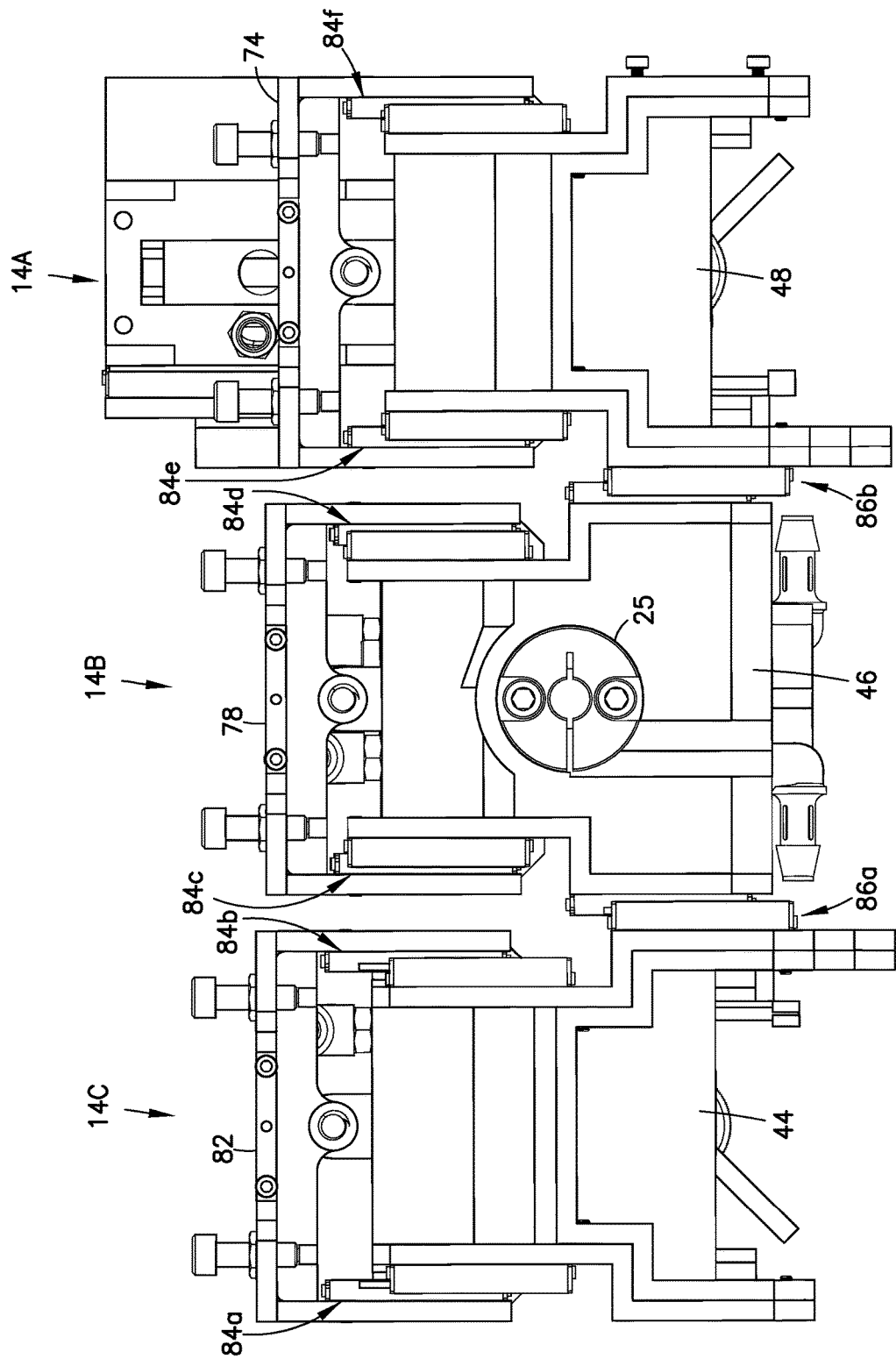
FIG. 5 is a diagram representing an elevational view of the inspection probe assembly depicted in FIG. 4.

FIGS. 4 and 5 are diagrams respectively representing an isometric view and an elevation view of the inspection probe assembly 14 in isolation and in accordance with one embodiment. In cases where the structure being inspected is a wing blade stiffener comprising a web and a flange that intersect at an intersection having left and right radiused portions, the inspection probe assembly 14 comprises three subassemblies: a web probe subassembly 14A, a flange probe subassembly 14B, and a radius probe subassembly 14C, as indicated in FIGS. 4 and 5.

In accordance with the embodiment depicted in FIG. 4, the flange probe subassembly 14B comprises a flange probe platform 46 clamped to rotatable shafts 28a and 28b (not shown in FIG. 4, but see FIG. 2A) by means of a pair of shaft collars 25 (only one of which is visible in FIGS. 4 and 5); the radius probe subassembly 14C comprises a radius probe platform 44 translatably coupled to one side of the flange probe platform 46 by means of a first pair of linear slides 86a (visible in FIG. 5) and 86c (visible in FIG. 4) to allow relative vertical displacement of the radius and flange probe subassemblies; and the web probe subassembly 14A comprises a web probe platform 48 translatably coupled to the other side of the flange probe platform 46 by means of a second pair of linear slides 86b (visible in FIG. 5) and 86d (visible in FIG. 4) to allow relative vertical displacement of the web and flange probe subassemblies. The linear slides 86a-86d allow the radius probe platform 44 and the web probe platform 48 to adjust their vertical positions relative to the flange probe platform 46 as the inspection probe assembly 14 travels along the length of an elongated composite member. (As used in this and subsequent paragraphs, the terms "horizontal" and "vertical" are with respect to the frame of reference of the flange probe platform 46.)

Referring again to FIG. 4, the flange probe subassembly 14B further comprises a pair of slide bracket assemblies 76 and 78 translatably coupled to the flange probe platform 46; the radius probe subassembly 14C further comprises a pair of slide bracket assemblies 80 and 82 translatably coupled to the radius probe platform 44; and the web probe subassembly 14A further comprises a pair of slide bracket assemblies 72 and 74 translatably coupled to the web probe platform 46. Each slide bracket assembly is translatably coupled to the associated probe platform by means of pairs of linear slides.

FIG. 5 shows a pair of linear slides 84a and 84b which translatably couple slide bracket assembly 82 to radius probe platform 44; a pair of linear slides 84c and 84d which translatably couple slide bracket assembly 78 to flange probe platform 46; and a pair of linear slides 84e and 84f which translatably couple slide bracket assembly 74 to web probe platform 48. FIG. 4 shows a pair of linear slides 84g and 84h which translatably couple slide bracket assembly 80 to radius probe platform 44; a pair of linear slides 84i and 84j which translatably couple slide bracket assembly 76 to flange probe platform 46; and a pair of linear slides 84k and 84l which translatably couple slide bracket assembly 72 to web probe platform 48.

Referring again to FIG. 4, the flange probe subassembly 14B further comprises a first dry acoustic couplant housing 54 translatably coupled to slide bracket assembly 78 by means of linear slides 88c and 88d; and a second dry acoustic couplant housing 56 translatably coupled to slide bracket assembly 76 by means of linear slides 88i and 88j. The radius probe subassembly 14C further comprises a first radius probe housing 50 translatably coupled to slide bracket assembly 82 by means of linear slides 88a and 88b; and a second radius probe housing 52 translatably coupled to slide bracket assembly 80 by means of linear slides 88g and 88h. The web probe subassembly 14A further comprises a first pivot support carriage 58 translatably coupled to slide bracket assembly 74 by means of linear slides 88e and 88f; and a second pivot support carriage 60 translatably coupled to slide bracket assembly 72 by means of linear slides 88k and 88l.

Although not shown in the drawings, springs are provided which urge the slide bracket assemblies to translate vertically toward the respective probe platforms, so that the radius probe housings 50, 52, the dry acoustic couplant housings 54 and 56, and the pivot support carriages 58, 60 clamp the blade stiffener flange. Springs are also provided to urge the radius probe housings 50, 52, the dry acoustic couplant housings 54 and 56, and the pivot support carriages 58, 60 to translate horizontally toward the blade stiffener web. Translation toward the blade stiffener web is limited in each case by a bolt 182 (see, e.g., FIGS. 4 and 8) which has a threaded portion threadably engaged with a threaded bore in a respective slide bracket assembly and an unthreaded portion that passes through a clearance hole in a Y limit sleeve 180 (see FIG. 6A). Bolt 182 is not threadably engaged to Y limit sleeve 180. The Y limit sleeve 180 functions as a stopper. For example, the radius probe housing 50 cannot slide past the head of the bolt 182. The minimum gap between the two radius probe housings 50 and 52 can be adjusted by loosening/tightening the bolts 182. This allows the probe to run onto the end of a blade stiffener more easily by adjusting the gap to closely match the thickness of the blade stiffener web.

Still referring to FIG. 4, the web probe subassembly 14A further comprises a first web probe housing 62 rotatably coupled to the first pivot support carriage 58 and a second web probe housing 64 rotatably coupled to the second pivot support carriage 60. In addition, the first and second web probe housings 62 and 64 are indirectly translatably coupled to each other by means of an L-shaped bracket 66 comprising a first leg 66a and a second leg 66b that form a right angle. The first web probe housing 62 is translatably coupled to the first leg 66a of the L-shaped bracket 66 by means of a linear slide 68 to enable translation along a line parallel to the first leg 66a; the second web probe housing 64 is translatably coupled to the second leg 66b of the L-shaped bracket 66 by means of a linear slide 70 to enable translation along a line parallel to the second leg 66b.

In accordance with the embodiment depicted in FIGS. 4 and 5, each probe subassembly comprises a respective pair of ultrasonic transducer arrays. The web probe subassembly 14A comprises a first pair of linear ultrasonic transducer arrays respectively housed in the web probe housings 62 and 64 (see linear ultrasonic transducer arrays 90a and 90b in FIG. 7). The radius probe subassembly 14C comprises a pair of curved ultrasonic transducer arrays respectively housed in the radius probe housings 50 and 52 (see curved ultrasonic transducer arrays 92a and 92b in FIG. 8). The flange probe subassembly 14B comprises a second pair of linear ultrasonic transducer arrays housed in the flange probe platform 46 (see linear ultrasonic transducer array 96a in FIG. 9A and linear ultrasonic transducer array 96b in FIG. 9B).

Figure 6:
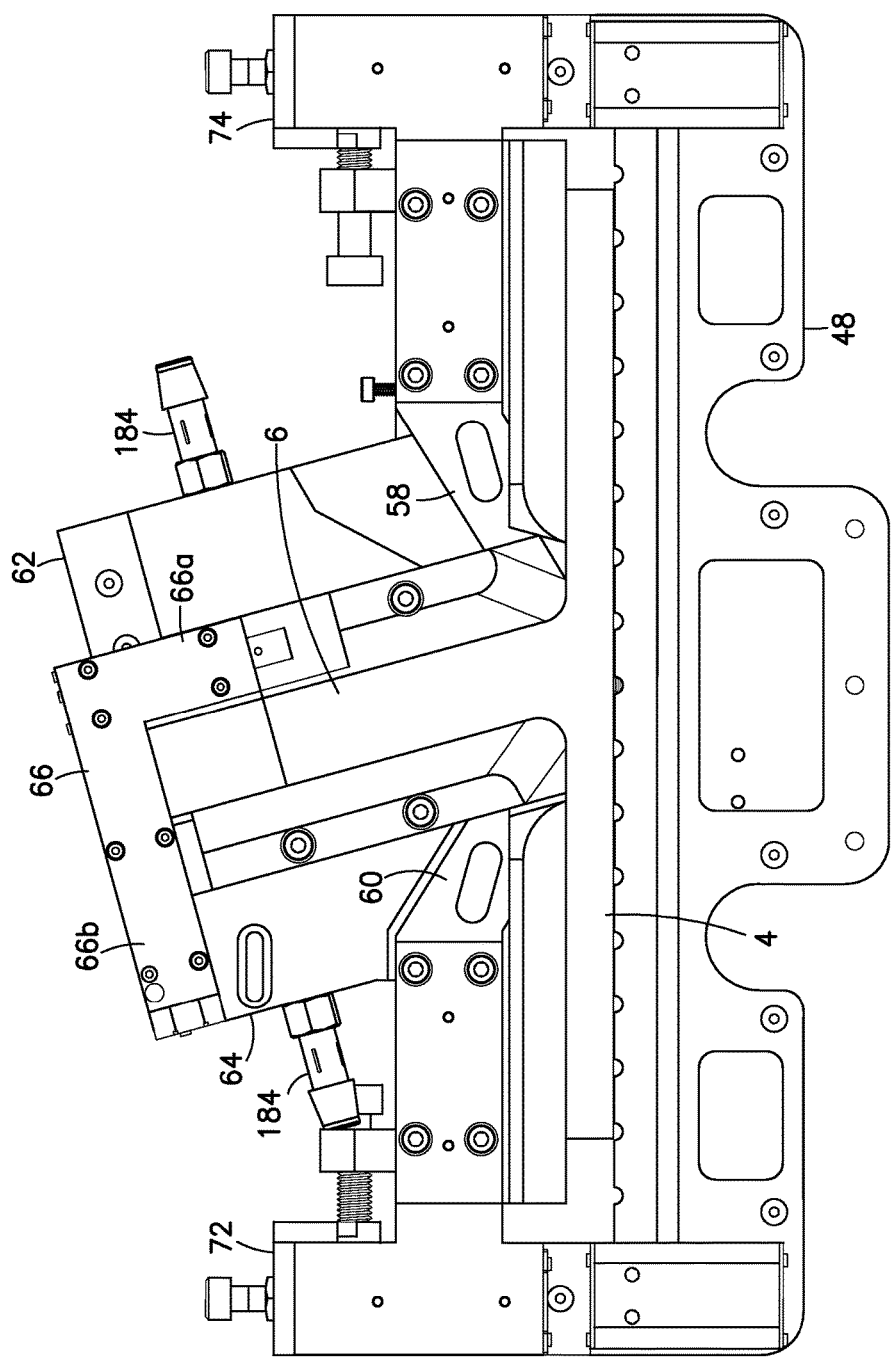
FIG. 6 is a diagram representing a side elevational view of a web probe subassembly incorporated in the inspection probe assembly depicted in FIG. 4.
Figure 7:
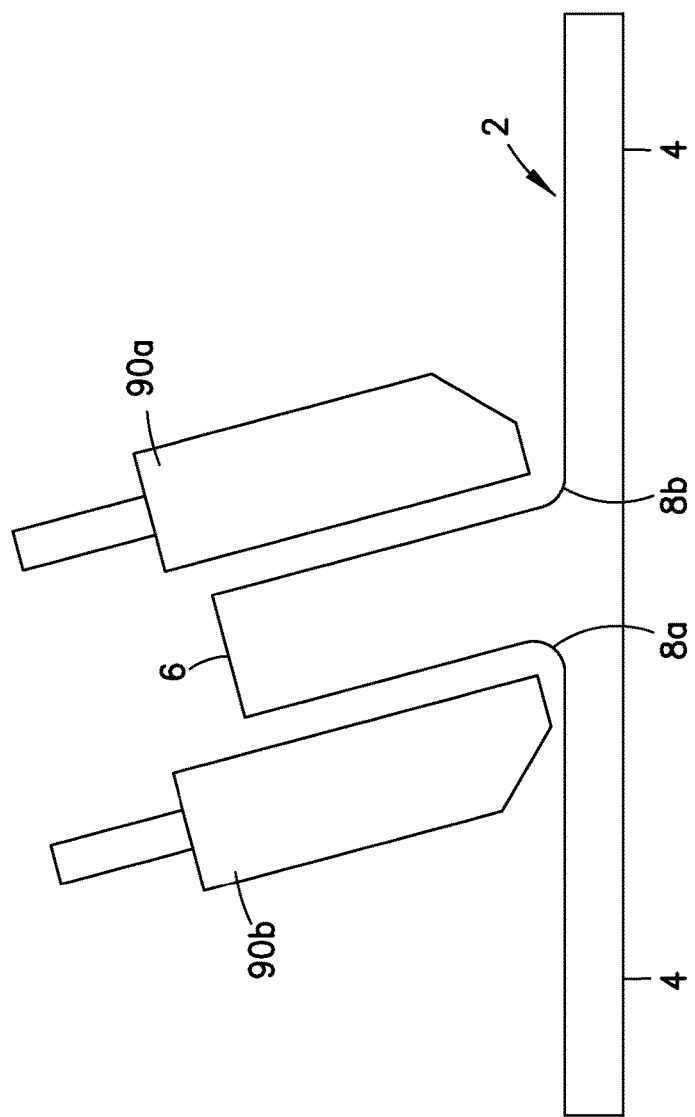
FIG. 7 is a diagram representing an elevational view of a pair of linear ultrasonic transducer arrays disposed on opposite sides of a web of a blade stiffener.

FIG. 6 is a diagram representing a side elevational view of the web probe subassembly 14A during inspection of a blade stiffener web 6 which is not perpendicular to the blade stiffener flange 4. Similarly, FIG. 7 is a diagram representing an elevational view of a pair of linear ultrasonic transducer arrays 90a and 90b disposed on opposite sides of a blade stiffener web 6 which is not perpendicular to the blade stiffener flange 4. It should be understood that the web probe housing 62 depicted in FIG. 6 houses the linear ultrasonic transducer array 90a depicted in FIG. 7 to form a first web probe, while the web probe housing 64 depicted in FIG. 6 houses the linear ultrasonic transducer array 90b depicted in FIG. 7 to form a second web probe. As seen in FIG. 6, water is provided inside the web probe housings 62 and 64 by way of respective water fittings 184.

Figure 6A:
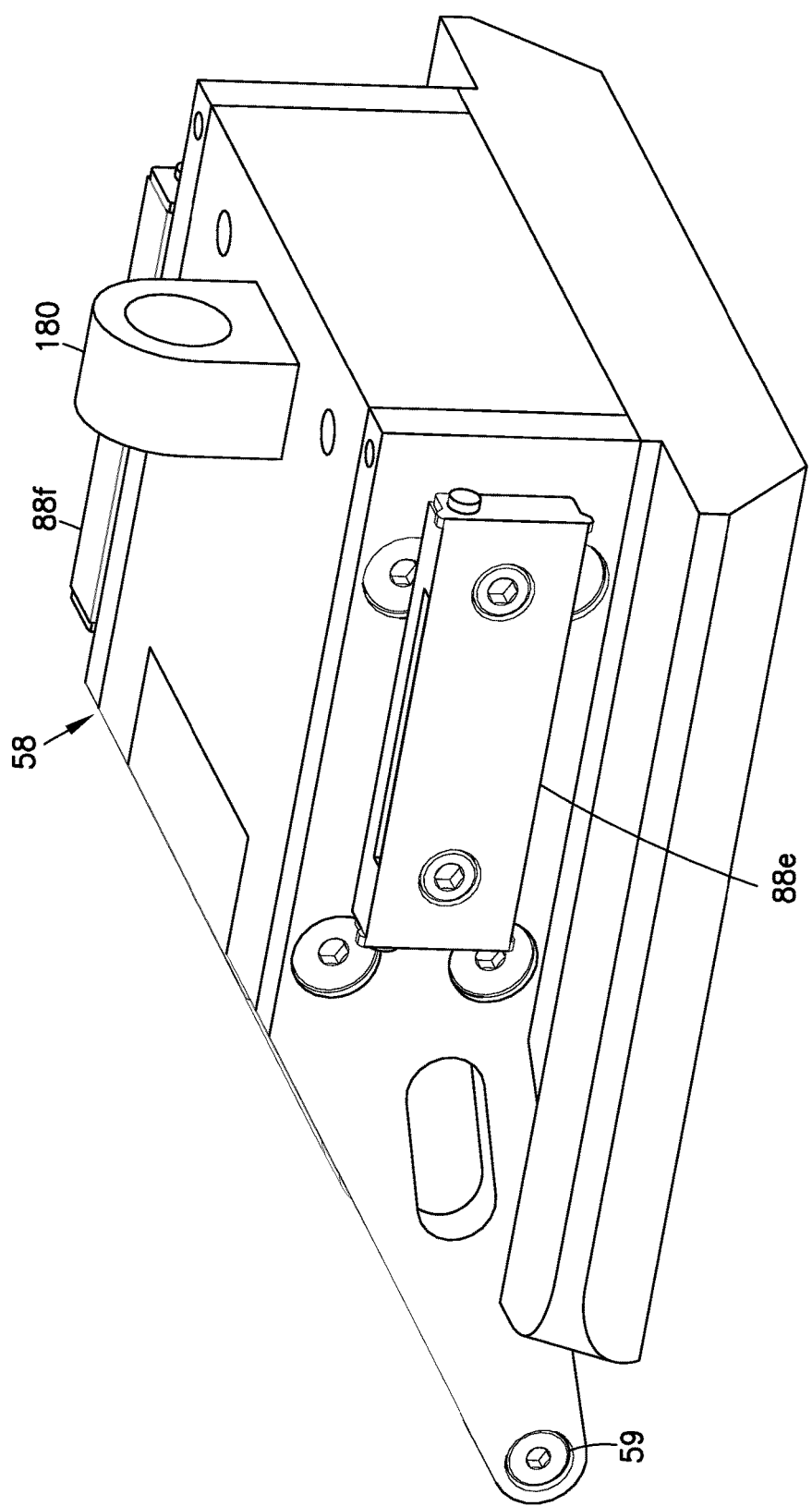
FIG. 6A is a diagram representing an isometric view of a pivot support carriage incorporated in the web probe subassembly depicted in FIG. 6.

As seen in FIG. 6, the web probes can rotate to adjust to a changing web-flange angle of the blade stiffener. This angle changes along the length of the part. The web probes follow the changing web-flange angle. More specifically, the web probe housings 62 and 64 rotate in tandem by the same angle about first and second axes of respective pairs of pivot joints (not visible in FIG. 6) which rotatably couple the web probe housings 62 and 64 to the pivot support carriages 58 and 60 respectively. FIG. 6A shows the pivot support carriage 58 having a pair of coaxial pivot points 59, only one of which is visible in the drawing. The pivot support carriage 60 seen in FIG. 6 has a similar pair of coaxial pivot points. The pivot points may take the form of revolute joints.

As seen in FIG. 7, the linear ultrasonic transducer arrays 90a and 90b stay in mutually parallel relationship despite rotation of the web probe housings 62 and 64. In addition, the width of the gap between the mutually parallel linear ultrasonic transducer arrays 90a and 90b will adjust to the varying thickness of the blade stiffener web 6 due to the ability of the pivot support carriages 58 and 60 (see FIG. 6) to translate horizontally toward or away from each other. Furthermore, in cases where the blade stiffener has a constant thickness but a non-zero curvature in a horizontal plane, the pivot support carriages 58 and 60 can translate horizontally in the same direction to compensate for that web curvature.

The linear ultrasonic transducer arrays 90a and 90b (see FIG. 7) can be operated in a pitch echo mode to ultrasonically inspect the left and right sides of web 6 of a blade stiffener. During scanning, the L-shaped bracket 66 (in conjunction with linear slides 68 and 70 depicted in FIG. 4) allows the linear ultrasonic transducer arrays 90a and 90b to move up and down (parallel to the blade stiffener web 6) independently and move side to side (parallel to the blade stiffener flange 4) independently As the web probe housings 62 and 64 (see FIG. 6) rotate in tandem and/or move up/down and/or move closer together/further apart, the L-shaped bracket 66 maintains the parallelism of the linear ultrasonic transducer arrays 90*a* and 90*b*. More specifically, the L-shaped bracket 66 can translate relative to web probe housing 62 along an axis parallel to the linear ultrasonic transducer array 90*a* due to the translatable coupling of leg 66*a* to web probe housing 62. In addition, the L-shaped bracket 66 can translate along an axis perpendicular to the linear ultrasonic transducer array 90*b* due to the translatable coupling of leg 66*b* to web probe housing 64. The surface area on opposite sides of the blade stiffener web 6 gets smaller or larger depending on the web-flange angle. When the web-flange angle changes from acute to obtuse, the coverage of this area changes from one linear ultrasonic transducer array to the other.

Figure 8:
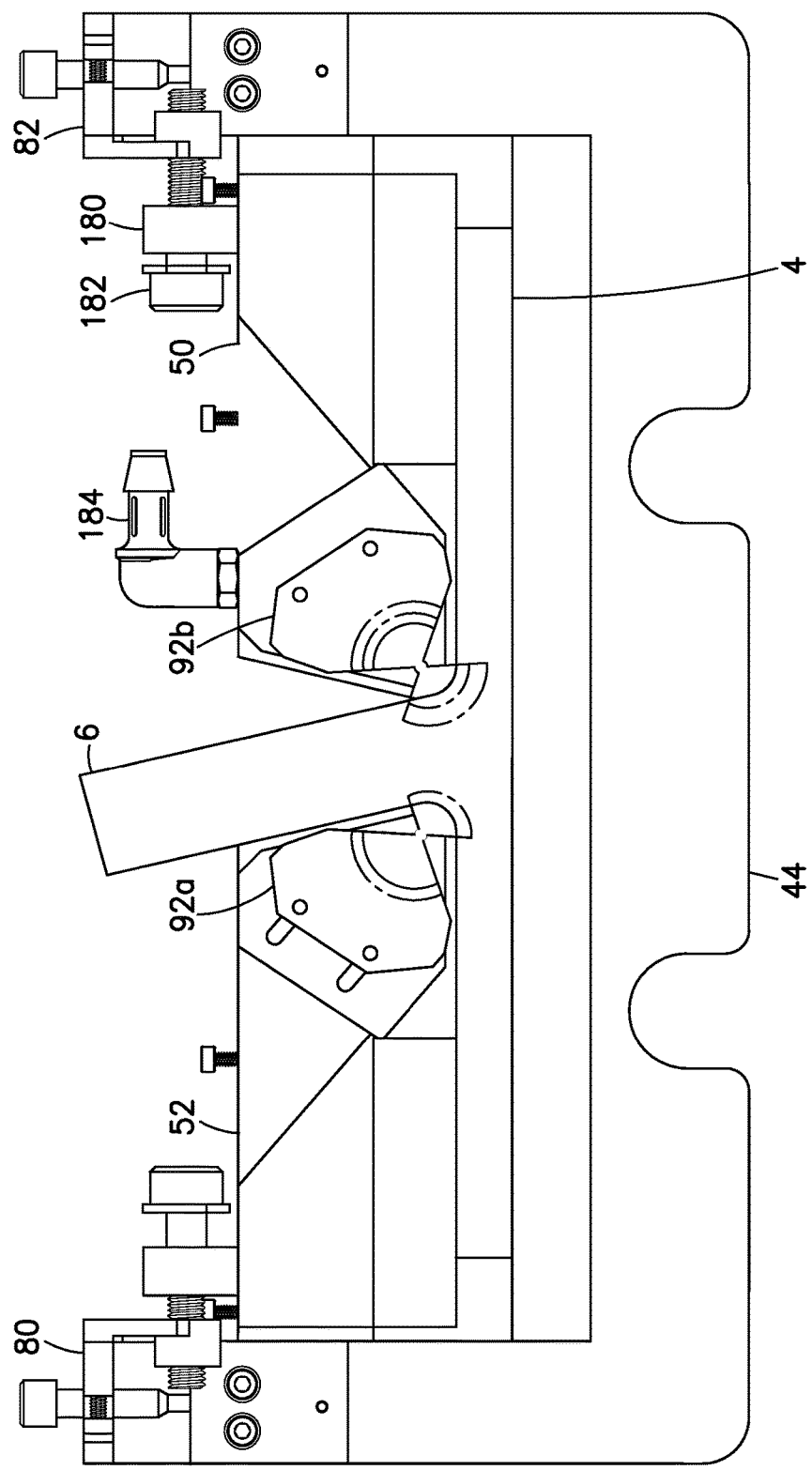
FIG. 8 is a diagram representing a sectional view of a radius probe subassembly incorporated in the inspection probe assembly depicted in FIG. 4.

FIG. 8 shows a sectional view of the radius probe subassembly 14C incorporated in the inspection probe assembly 14 depicted in FIG. 4. As previously described, the radius probe subassembly 14C comprises: a pair of slide bracket assemblies 80 and 82 translatably coupled to the radius probe platform 44; a first radius probe housing 50 translatably coupled to slide bracket assembly 82; and a second radius probe housing 52 translatably coupled to slide bracket assembly 80. A pair of curved ultrasonic transducer arrays 92*a* and 92*b* are respectively housed inside radius probe housings 52 and 50 to form first and second radius probes for respectively scanning the left and right radiused portions of a blade stiffener. Springs (not shown in FIG. 8) are provided to urge slide bracket assemblies 80 and 82 to translate downward and urge radius probe housings 50 and 52 to translate laterally toward the blade stiffener web, as a result of which the curved ultrasonic transducer arrays 92*a* and 92*b* will be disposed near the left and right radiused portions respectively. The curved ultrasonic transducer arrays 92*a* and 92*b* can be operated in a pitch echo mode to ultrasonically inspect the left and right radiused portions of the blade stiffener. Water is provided inside the radius probe housings 50 and 52 by way of respective water fittings 184 (only one of which is shown in FIG. 8).

Figure 9:
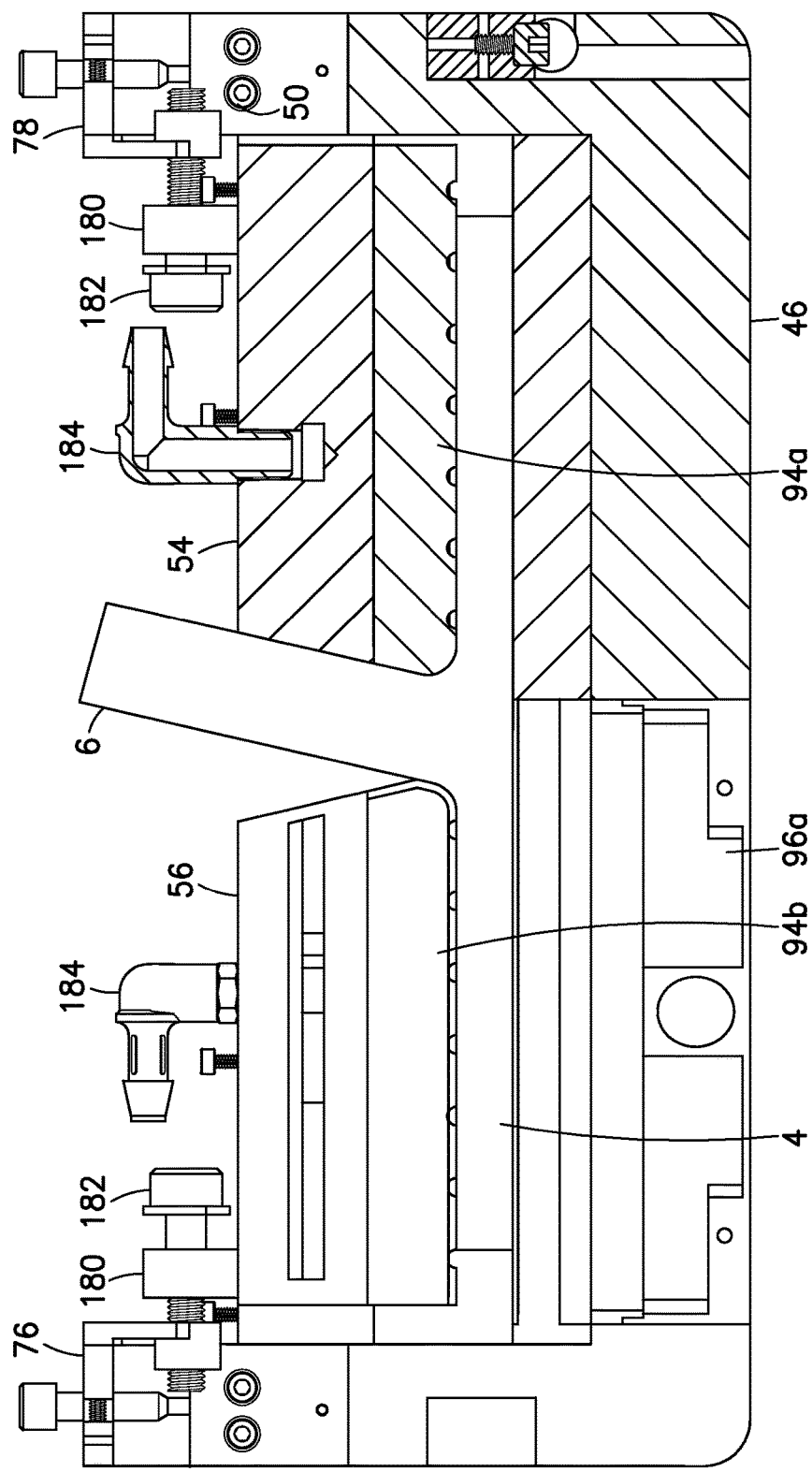
FIGS. 9A and 9B are respective sectional views of a flange probe subassembly incorporated in the inspection probe assembly depicted in FIG. 4.

FIGS. 9A and 9B are respective sectional views of the flange probe subassembly 14B incorporated in the inspection probe assembly 14 depicted in FIG. 4. In FIG. 9A, the section is taken through the first linear ultrasonic transducer array; in FIG. 9B, the section is taken through a second linear ultrasonic transducer array. As previously described, the flange probe subassembly 14B comprises a flange probe platform 46 which houses a pair of linear ultrasonic transducer arrays 96*a* (see FIG. 9A) and 96*b* (see FIG. 9B) which partly overlap underneath the web-flange intersection of the blade stiffener. In the alternative, a single linear ultrasonic transducer array of sufficient length could be substituted for the linear ultrasonic transducer arrays 96*a* and 96*b*, so long as the entire width of the blade stiffener flange 4 is covered.

In the implementation depicted in FIGS. 9A and 9B, the linear ultrasonic transducer arrays 96*a* and 96*b* are acoustically coupled by water to the bottom surface of the blade stiffener flange 4. In addition, the upper surfaces of the blade stiffener flange 4 are in contact with respective blocks 94*a* and 94*b* of dry acoustic couplant elastomeric material respectively housed in the dry acoustic couplant housings 54 and 56. The dry acoustic couplant elastomeric material (e.g., Aqualene Rubber commercially available from Innovation Polymers, Kitchener, Ontario, Canada) has an acoustic velocity and an acoustic impedance nearly the same as water. The blocks 94*a* and 94*b* of dry acoustic couplant elastomeric material (which mimics the effect of water on ultrasound waves) act as delay lines by enabling ultrasound waves to pass through. The system detects getting reflections from the upper surfaces of the blade stiffener flange 4 during pulse echo inspection. The impedance mismatch of the composite material relative to the water creates this reflection. The elastomeric material serves to mimic the impedance of water so the reflection from the upper surface of the blade stiffener flange 4 looks the same as if water were on the back side of the flange.

The benefits of the elastomeric material are twofold. First, it greatly reduces the amount of water needed on top of the flange 4. To flood the top of a wide (e.g., 9-inch) flange would require a very large amount of water and increase the size of water pumps, hoses, etc. Second, the elastomeric material creates a calm and stable thin film water source for the outer edge of the flange 4. This allows for fine edge resolution in the ultrasonic data without seeing signal shifts from water turbulence on the edge of the part.

As seen in FIG. 9A, water is provided inside the dry acoustic couplant housings 54 and 56 by way of respective water fittings 184. The presence of the dry acoustic couplant elastomeric material reduces the size of the water column. Good acoustic coupling is maintained by locally flooding both sides of the part with water inside the perimeters of the respective probes.

As is well known to persons skilled in the art of ultrasonic inspection, water can be fed through one or more supply lines, through the water fittings 184 and into one or more recesses, such as defined channels or manifolds, a central cavity, or similar openings that permit the flow of water through the housings. A fluid manifold for an inspection probe is the structure of one or more internal water passages to feed the interfaces between the ultrasonic transducer arrays and the part being inspected, thereby coupling ultrasonic signals between the ultrasonic transducer arrays and the part. This process is known as fluid coupling. A fluid manifold may be formed of any number of shapes and merely represents a defined passage from a fluid inlet port to an area through which ultrasound waves propagate for controlling the flow of fluid from the fluid inlet port to the area through which ultrasound waves propagate.

Because contact with a surface of the inspected part may be interrupted, such as along an edge of the part being inspected, the ultrasonic inspection apparatus disclosed herein uses special fluid manifolds in accordance with a so-called "bubbler method" wherein respective bubbler shoes disperse the fluid around each ultrasonic transducer to independently couple the signal from each ultrasonic transducer to the confronting surface area of the part under inspection, rather than using a single cavity to couple all of the ultrasonic transducers. Bubbler shoes are described further, for example, in U.S. Pat. No. 7,337,673, the disclosure of which is incorporated by reference in its entirety herein. By individually coupling each transducer to the surface of the part, the bubbler shoe compensates for when a portion of the probe travels off an edge of the structure. In such a manner, only the transducers off the edge of the structure will lose the coupling with the surface, but the transducers remaining over the surface of the structure will continue to be independently coupled.

Figure 10:
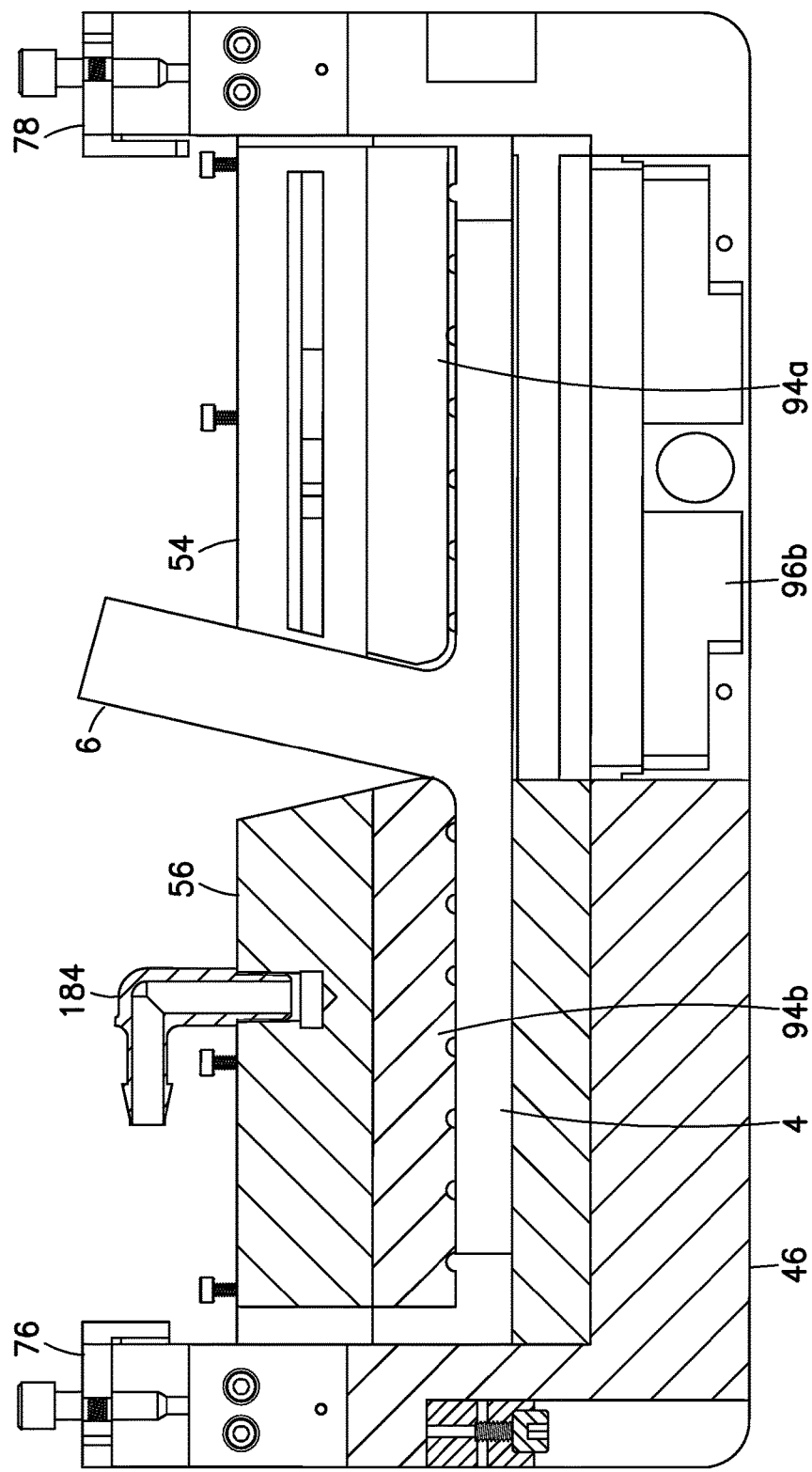
FIG. 10 is a diagram representing an isometric view of a run-on tool mounted to an outboard end of a blade stiffener.
Figure 11:
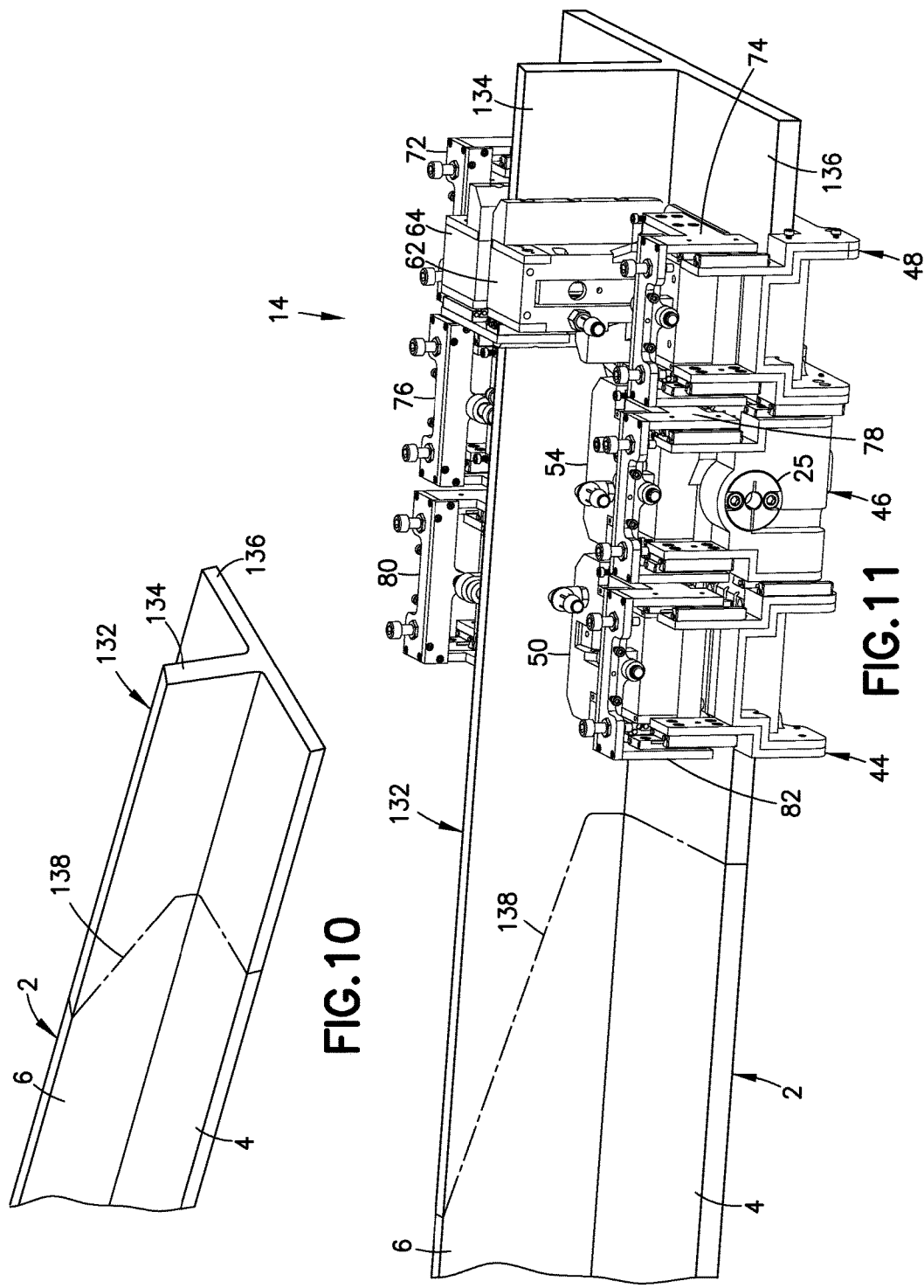
FIG. 11 is a diagram representing an isometric view of the inspection probe assembly depicted in FIG. 4 mounted to the run-on tool depicted in FIG. 10.

When not inspecting a blade stiffener, the inspection probe assembly 14 may be parked on a run-on tool 132 that is designed to serve as an extension of the blade stiffener 2, as depicted in FIGS. 10 and 11. As best seen in FIG. 10, the run-on tool 132 comprises a run-on tool web 134 and a run-on tool flange 136. In addition, the run-on tool 132 may have a web-to-flange angle that matches the web-to-flange angle of an outboard end of the blade stiffener 2. The probe assembly is designed to accept a range of part thickness changes. The range should envelope the outboard end of the stiffeners. The number of run-on tools would likely accommodate the ranges of web to flange angles. The result is a seamless interface 138 that enables the inspection probe assembly 14 to smoothly ride onto the blade stiffener 2 at the start of an inspection procedure. This keeps the water acoustic coupling stable, maintains edge alignment, and allows for a smooth transition as the inspection probe assembly 14 moves from the run-on tool 132 to the blade stiffener 2.

Figure 12:
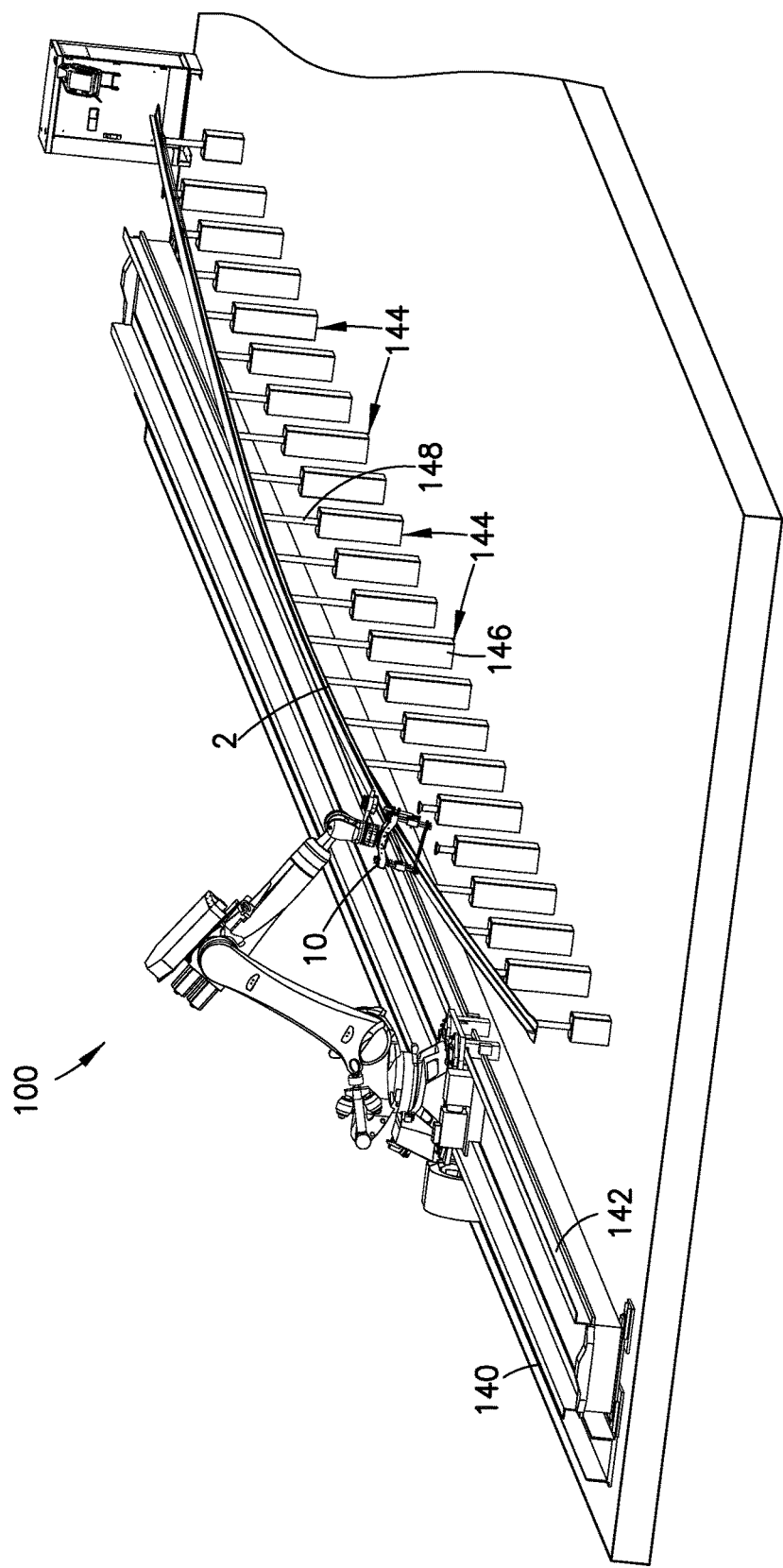
FIG. 12 is a diagram representing an isometric view of a workcell for automated single-pass ultrasonic inspection of a curved blade stiffener supported by retractable holding fixtures in accordance with one embodiment.

FIG. 12 is a diagram representing an isometric view of a workcell for automated single-pass ultrasonic inspection of a curved blade stiffener 2 supported by a multiplicity of extendible/retractable holding fixtures 144 at spaced intervals along the blade stiffener 2. In accordance with one embodiment, each holding fixture comprises a plunger housing 146 and a plunger 148 which is extendible out of or retractable into the plunger housing 146. The respective amounts of extension of holding fixtures 144 can be controlled by a computer (not shown) such that each plunger contacts and thus supports a respective portion of the blade stiffener 2. The holding fixtures may be movable to support blade stiffeners having different lengths and contours.

The exemplary workcell shown in FIG. 12 further comprises a robot 100 of the type previously described with reference to FIG. 3, which robot 100 travels along a pair of mutually parallel linear tracks 140 and 142. As the robot moves along tracks 140 and 142, the ultrasonic inspection tool head 10 follows the blade stiffener 2, which may be curved as shown. As the ultrasonic inspection tool head 10 approaches each holding fixture 144 in turn, one or more optical detectors send a first signal to the computer, which is programmed to actuate retraction of that holding fixture, causing it to move out of the way. This allows the ultrasonic inspection tool head 10 to inspect the unsupported span without interference with the retracted holding fixture. After the inspection probe moves past the retracted holding fixture, one or more optical detectors send a second signal to the computer, which is further programmed to actuate extension of that holding fixture back to its original position. The computer-controlled holding fixtures can move in an orchestrated manner that provides a fully automated and seamless integrated solution that minimizes stresses induced on the part from an unsupported span or cantilever. The inspection probe assembly 14 may have enough compliance to keep load points on a blade stiffener less than 500μStrains during the inspection over a 10-foot unsupported span.

In an alternative embodiment, instead of a central control computer controlling the states of all holding fixture 144, each holding fixture may incorporate a respective microprocessor and one or more optical detectors to allow each holding fixture to operate independently.

The automated holding fixtures may be pre-programmed to different part options and adjusted by an automated means such as bar code recognition on a work order. The pre-programmed holding fixtures could be engaged by the robot program or a programmable logic controller device. The holding fixtures could be individual robots themselves or simple pogo-type holding fixtures of the type depicted in FIG. 12.

Figure 13:
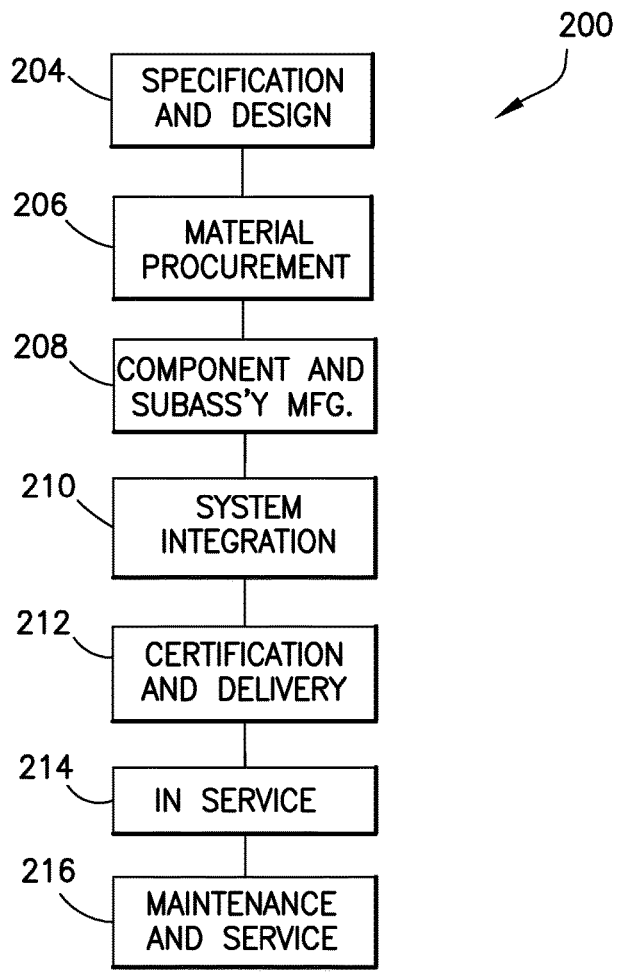
FIG. 13 is a flow diagram of an aircraft production and service methodology.
Figure 14:
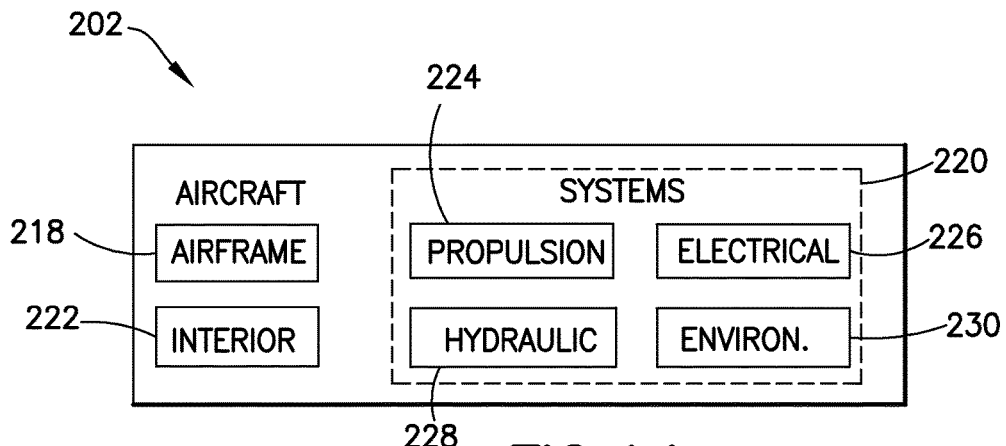
FIG. 14 is a block diagram showing systems of an aircraft.

The system and method disclosed above may be employed in an aircraft manufacturing and service method 200 as shown in FIG. 13 for inspecting parts of an aircraft 202 as shown in FIG. 14. During pre-production, exemplary method 200 may include specification and design 204 of the aircraft 202 and material procurement 206. During production, component and subassembly manufacturing 208 and system integration 210 of the aircraft 202 takes place. Thereafter, the aircraft 202 may go through certification and delivery 212 in order to be placed in service 214. While in service by a customer, the aircraft 202 is scheduled for routine maintenance and service 216 (which may also include modification, reconfiguration, refurbishment, and so on).

Each of the processes of method 200 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 13, the aircraft 202 produced by exemplary method 200 may include an airframe 218 (comprising, e.g., a fuselage, frames, stiffeners, wing boxes, etc.) with a plurality of systems 220 and an interior 222. Examples of high-level systems 220 include one or more of the following: a propulsion system 224, an electrical system 226, a hydraulic system 226, and an environmental control system 230. Any number of other systems may be included. Although an aerospace example is shown, the principles disclosed herein may be applied to other industries, such as the automotive industry.

Apparatus and methods embodied herein may be employed during any one or more of the stages of the production and service method 200. For example, elongated composite members fabricated during production process 208 may be inspected using the inspection system disclosed herein. Also, one or more apparatus embodiments, method embodiments, or a combination thereof may be utilized during the production stages 208 and 210, for example, by substantially expediting assembly of or reducing the cost of an aircraft 202. Similarly, one or more of apparatus embodiments, method embodiments, or a combination thereof may be utilized while the aircraft 202 is in service, for example and without limitation, during maintenance and service 216.

While ultrasonic inspection systems have been described with reference to various embodiments, it will be understood by those skilled in the art that various changes may be made and equivalents may be substituted for elements thereof without departing from the scope of the teachings herein. In addition, many modifications may be made to adapt the teachings herein to a particular situation without departing from the scope thereof. Therefore it is intended that the claims not be limited to the particular embodiments disclosed herein.

The invention claimed is:
1. An apparatus comprising:
a frame;
first and second rotatable shafts which are mutually coaxial and rotatable relative to said frame; and
a probe housing assembly clamped to said first and second rotatable shafts, wherein said probe housing assembly comprises:
a first probe platform clamped to said first and second rotatable shafts;
a second probe platform;
first and second linear slides configured to translatably couple said second probe platform to said first probe platform;
a third probe platform; and third and fourth linear slides configured to translatably couple said third probe platform to said first probe platform.

2. The apparatus as recited in claim 1, wherein said frame comprises first through fourth guide shafts, the apparatus further comprising a first bearing block assembly translatably coupled to said first and second guide shafts, and a second bearing block assembly translatably coupled to said third and fourth guide shafts, wherein said first rotatable shaft is rotatably coupled to said first bearing block assembly, and said second rotatable shaft is rotatably coupled to said second bearing block assembly.

3. The apparatus as recited in claim 1, further comprising a gimbal assembly disposed between said frame and a tool-side connector configured to be attached to a connector of a robot, said gimbal assembly comprising a revolute joint supported by said tool-side connector, a thrust bearing, and fifth and sixth linear slides configured to translatably couple said thrust bearing to said revolute joint.

4. The apparatus as recited in claim 1, further comprising:
a first web probe translatably coupled to one of said first through third probe platforms for translation along first and second axes which are mutually perpendicular, said first web probe comprising a first linear ultrasonic transducer array;
a second web probe translatably coupled to said one of said first through third probe platforms for translation along third and fourth axes which are mutually perpendicular, said second web probe comprising a second linear ultrasonic transducer array which is parallel to said first linear ultrasonic transducer array.

5. The apparatus as recited in claim 4, wherein said first web probe is rotatably coupled to said one of said first through third probe platforms for rotation about a fifth axis which is perpendicular to said first and second axes, and said second web probe is rotatably coupled to said one of said first through third probe platforms for rotation about a sixth axis which is perpendicular to said third and fourth axes, the apparatus further comprising:
an L-shaped member comprising first and second legs that form a right angle;
a fifth linear slide configured to translatably couple said first leg of said L-shaped member to said first web probe to enable translation along a length of said first leg; and
a sixth linear slide configured to translatably couple said second leg of said L-shaped member to said first web probe to enable translation along a length of said second leg,
wherein said first and second linear ultrasonic transducer arrays stay mutually parallel and displace relative to each other during rotation in tandem about said first and second axes respectively.

6. The apparatus as recited in claim 1, further comprising:
a first radius probe translatably coupled to one of said first through third probe platforms for translation along first and second axes which are mutually perpendicular, said first radius probe comprising a first curved ultrasonic transducer array; and
a second radius probe translatably coupled to said one of said first through third probe platforms for translation along third and fourth axes which are mutually perpendicular, said second radius probe comprising a second curved ultrasonic transducer array.

7. The apparatus as recited in claim 1, further comprising:
a linear ultrasonic transducer array housed in one of said first through third probe platforms; and
a dry acoustic couplant material separated from said linear ultrasonic transducer array by a gap,
wherein said probe housing assembly further comprises:
a dry acoustic couplant housing translatably coupled to said one of said first through third probe platforms for translation along first and second axes which are mutually perpendicular, said dry acoustic couplant housing supporting said dry acoustic couplant material.

8. The apparatus as recited in claim 1, further comprising:
a first web probe translatably coupled to one of said first through third probe platforms for translation along first and second axes which are mutually perpendicular, said first web probe comprising a first linear ultrasonic transducer array;
a second web probe translatably coupled to said one of said first through third probe platforms for translation along third and fourth axes which are mutually perpendicular, said second web probe comprising a second linear ultrasonic transducer array which is parallel to said first linear ultrasonic transducer array;
a first radius probe translatably coupled to another of said first through third probe platforms for translation along fifth and sixth axes which are mutually perpendicular, said first radius probe comprising a first curved ultrasonic transducer array; and
a second radius probe translatably coupled to said another of said first through third probe platforms for translation along seventh and eighth axes which are mutually perpendicular, said second radius probe comprising a second curved ultrasonic transducer array.

9. The apparatus as recited in claim 8, further comprising:
a third linear ultrasonic transducer array housed in a further one of said first through third probe platforms; and
a dry acoustic couplant material separated from said third linear ultrasonic transducer array by a gap,
wherein said probe housing assembly further comprises:
a dry acoustic couplant housing translatably coupled to said further one of said first through third probe platforms for translation along ninth and tenth axes which are mutually perpendicular, said dry acoustic couplant housing supporting said dry acoustic couplant material.

10. The apparatus as recited in claim 9, wherein said first, second and third linear ultrasonic transducer arrays and said first and second curved ultrasonic transducer arrays are arranged so that said first and second linear ultrasonic transducer arrays can interrogate a web portion of an elongated composite member having a generally T-shaped profile, while said first and second curved ultrasonic transducer arrays can interrogate respective radiused portions of the elongated composite member, and said third linear ultrasonic transducer array can interrogate a flange portion of the elongated composite member in a single pass.

11. An apparatus comprising:
a probe housing assembly;
a first web probe rotatably coupled to said probe housing assembly for rotation about a first axis, said first web probe comprising a first linear ultrasonic transducer array;
a second web probe rotatably coupled to said probe housing assembly for rotation about a second axis which is parallel to said first axis, said second web probe comprising a second linear ultrasonic transducer array which is parallel to said first linear ultrasonic transducer array;
an L-shaped member comprising first and second legs that form a right angle;

a first linear slide configured to translatably couple said first leg of said L-shaped member to said first web probe to enable translation along a length of said first leg; and a second linear slide configured to translatably couple said second leg of said L-shaped member to said first web probe to enable translation along a length of said second leg, wherein said first and second linear ultrasonic transducer arrays stay mutually parallel and displace relative to each other during rotation in tandem about said first and second axes respectively.

12. The apparatus as recited in claim 11, wherein said probe housing assembly comprises:

a left pivot support carriage which is rotatably coupled to said first web probe;

a first slide bracket assembly;

third and fourth linear slides configured to translatably couple said first slide bracket assembly to said left pivot support carriage;

a right pivot support carriage which is rotatably coupled to said second web probe;

a second slide bracket assembly; and fifth and sixth linear slides configured to translatably couple said second slide bracket assembly to said right pivot support carriage;

wherein said left and right pivot support carriages are slidable along third and fourth axes respectively, said third and fourth axes being perpendicular to said first and second axes.

13. The apparatus as recited in claim 12, wherein said probe housing assembly further comprises:

a web probe platform;

seventh and eighth linear slides configured to translatably couple said first slide bracket assembly to said web probe platform; and ninth and tenth linear slides configured to translatably couple said second slide bracket assembly to said web probe platform, wherein said first and second slide bracket assemblies are slidable along fifth and sixth axes respectively, said fifth axis being perpendicular to said first and third axes, and said sixth axis being perpendicular to said second and fourth axes.

14. The apparatus as recited in claim 13, further comprising a frame and first and second rotatable shafts which are mutually coaxial and rotatable relative to said frame, wherein said probe housing assembly is clamped to said first and second rotatable shafts.

15. The apparatus as recited in claim 14, wherein said frame comprises first through fourth guide shafts, the apparatus further comprising a first bearing block assembly translatably coupled to said first and second guide shafts, and a second bearing block assembly translatably coupled to said third and fourth guide shafts, wherein said first rotatable shaft is rotatably coupled to said first bearing block assembly, and said second rotatable shaft is rotatably coupled to said second bearing block assembly.

16. The apparatus as recited in claim 14, wherein said probe housing assembly further comprises a flange probe platform clamped to said first and second rotatable shafts; and eleventh and twelfth linear slides configured to translatably couple said web probe platform to said flange probe platform, the apparatus further comprising a third linear ultrasonic transducer array housed in said flange probe platform.

17. The apparatus as recited in claim 16, further comprising a dry acoustic couplant material separated from said third linear ultrasonic transducer array by a gap, wherein said probe housing assembly further comprises:

a dry acoustic couplant housing which supports said dry acoustic couplant material;

a third slide bracket assembly;

thirteenth and fourteenth linear slides configured to translatably couple said third slide bracket assembly to said dry acoustic couplant housing; and fifteenth and sixteenth linear slides configured to translatably couple said third slide bracket assembly to said flange probe platform.

18. The apparatus as recited in claim 16, wherein said probe housing assembly further comprises a radius probe platform, and thirteenth and fourteenth linear slides configured to translatably couple said radius probe platform to said flange probe platform, the apparatus further comprising first and second radius probes translatably coupled to said radius probe platform, wherein said first radius probe comprises a first curved ultrasonic transducer array, and said second radius probe comprises a second curved ultrasonic transducer array.

19. The apparatus as recited in claim 18, wherein said probe housing assembly further comprises:

a third slide bracket assembly;

thirteenth and fourteenth linear slides configured to translatably couple said third bracket assembly to said first radius probe; and fifteenth and sixteenth linear slides configured to translatably couple said third slide bracket assembly to said radius probe platform.

20. The apparatus as recited in claim 19, wherein said probe housing assembly further comprises:

a fourth slide bracket assembly;

seventeenth and eighteenth linear slides configured to translatably couple said fourth bracket assembly to said second radius probe; and nineteenth and twentieth linear slides configured to translatably couple said fourth slide bracket assembly to said radius probe platform.

21. The apparatus as recited in claim 14, further comprising a gimbal assembly disposed between said frame and a tool-side connector configured to be attached to a connector of a robot, said gimbal assembly comprising a revolute joint supported by said tool-side connector, a thrust bearing, and eleventh and twelfth linear slides configured to translatably couple said thrust bearing to said revolute joint.

* * * * *